United States Patent
Goldstein et al.

(10) Patent No.: US 12,194,156 B2
(45) Date of Patent: Jan. 14, 2025

(54) ACTIVE AGENT-CONTAINING MICROCAPSULES

(71) Applicant: Tagra Biotechnologies Ltd., Natania (IL)

(72) Inventors: Danny Goldstein, Kibbutz Dafna (IL); Olga Privalova, Kibbutz LeHavot HaBashan (IL); Lior Ben-Altabet, Kibbutz Dafna (IL); Yaniv Menachem, Moshav Dishon (IL); Hanan Haj, Rehaniya (IL); Shaher Duchi, Kfar Rama (IL)

(73) Assignee: Tagra Biotechnologies Ltd., Natania (IL)

( * ) Notice: Subject to any disclaimer, the term of this patent is extended or adjusted under 35 U.S.C. 154(b) by 0 days.

(21) Appl. No.: 15/123,639

(22) PCT Filed: Mar. 4, 2015

(86) PCT No.: PCT/IL2015/050236
§ 371 (c)(1),
(2) Date: Sep. 4, 2016

(87) PCT Pub. No.: WO2015/132792
PCT Pub. Date: Sep. 11, 2015

(65) Prior Publication Data
US 2017/0071865 A1    Mar. 16, 2017

Related U.S. Application Data

(60) Provisional application No. 61/947,683, filed on Mar. 4, 2014.

(51) Int. Cl.
*A61K 9/50* (2006.01)
*A61K 9/16* (2006.01)

(52) U.S. Cl.
CPC ............ *A61K 9/5078* (2013.01); *A61K 9/167* (2013.01)

(58) Field of Classification Search
None
See application file for complete search history.

(56) References Cited

U.S. PATENT DOCUMENTS

| | | | |
|---|---|---|---|
| 4,756,906 A | 7/1988 | Sweeny | |
| 5,897,868 A * | 4/1999 | Kobayashi | A61K 8/11 424/401 |
| 6,932,984 B1 | 8/2005 | Babtsov et al. | |
| 7,838,037 B2 | 11/2010 | Kvitnitsky et al. | |
| 2006/0078598 A1* | 4/2006 | Jobe | A23K 40/30 424/442 |
| 2006/0225617 A1* | 10/2006 | Ismail | A61K 8/29 106/504 |
| 2008/0081057 A1 | 4/2008 | Chevalier | |
| 2010/0330279 A1* | 12/2010 | Fogden | C09D 7/80 427/256 |

FOREIGN PATENT DOCUMENTS

| | | | |
|---|---|---|---|
| CN | 101309746 | | 11/2008 |
| CN | 102088946 | | 6/2011 |
| WO | WO 2007/023495 | | 3/2007 |
| WO | WO 2009/138978 | | 11/2009 |
| WO | WO 2012/156965 | | 11/2012 |
| WO | WO 2013/107354 | | 7/2013 |
| WO | WO 2013/107776 | * | 7/2013 |
| WO | WO 2015/132791 | | 9/2015 |
| WO | WO 2015/132792 | | 9/2015 |

OTHER PUBLICATIONS

International Preliminary Report on Patentability Dated Sep. 15, 2016 From the International Bureau of WIPO Re. Application No. PCT/IL2015/050235.
International Preliminary Report on Patentability Dated Sep. 15, 2016 From the International Bureau of WIPO Re. Application No. PCT/IL2015/050236.
International Search Report and the Written Opinion Dated Jun. 19, 2015 From the International Searching Authority Re. Application No. PCT/IL2015/050236.
International Search Report and the Written Opinion Dated May 21, 2015 From the International Searching Authority Re. Application No. PCT/IL2015/050235.
Communication Pursuant to Article 94(3) EPC Dated Jan. 2, 2018 From the European Patent Office Re. Application No. 15715858.5. (11 Pages).
Notification of Office Action and Search Report Dated Aug. 28, 2018 From the State Intellectual Property Office of the People's Republic of China Re. Application No. 201580021522.2. (10 Pages).
Communication Pursuant to Article 94(3) EPC Dated Jul. 20, 2018 From the European Patent Office Re. Application No. 15715858.5. (9 Pages).
Translation Dated Oct. 8, 2018 of Notification of Office Action Dated Aug. 28, 2018 From the State Intellectual Property Office of the People's Republic of China Re. Application No. 201580021522.2. (7 Pages).
Translation Dated Jul. 23, 2019 of Notification of Office Action Dated Jul. 15, 2019 From the State Intellectual Property Office of the People's Republic of China Re. Application No. 201580021522.2. (3 Pages).
Notification of Office Action Dated Jul. 15, 2019 From the State Intellectual Property Office of the People's Republic of China Re. Application No. 201580021522.2. (4 Pages).

(Continued)

*Primary Examiner* — Tigabu Kassa

(57) ABSTRACT

Multi-layer microcapsules comprising a core comprising one or more active agents and two or more shells comprised of a wall-forming polymeric material, an opaque substance and a fatty acid salt, which are rupturable upon rubbing or pressing on the skin, are disclosed. The microcapsules are characterized by improved lightness values (L*) and/or compatibility in aqueous solution-containing formulations. Cosmetic or cosmeceutic formulations comprising the microcapsules, which can be, for example, body skin care formulation or facial skin care formulations, are also provided.

20 Claims, 7 Drawing Sheets
(7 of 7 Drawing Sheet(s) Filed in Color)

(56) References Cited

OTHER PUBLICATIONS

Decision of Rejection Dated Jan. 7, 2020 From the State Intellectual Property Office of the People's Republic of China Re. Application No. 201580021522.2 and Its Translation Into English. (15 Pages).
Notification of Office Action Dated Jul. 15, 2021 From the State Intellectual Property Office of the People's Republic of China Re. Application No. 201580021522.2 and Its Translation into English. (42 Pages).
Requisition by the Examiner Dated Feb. 25, 2021 From the Innovation, Science and Economic Development Canada, Canadian Intellectual Property Office Re. Application No. 2,940,090. (5 Pages).
Grounds of Reasons for Rejection Dated Mar. 19, 2021 From the Korean Intellectual Property Office Re. Application No. 10-2016-7026833 and Its Translation Into English. (9 Pages).
Notification of Re-Examination and Search Report Dated Feb. 9, 2021 From the State Intellectual Property Office of the People's Republic of China Re. Application No. 201580021522.2. (10 Pages).
Translation Dated Feb. 23, 2021 of Notification of Re-Examination Dated Feb. 9, 2021 From the State Intellectual Property Office of the People's Republic of China Re. Application No. 201580021522.2. (10 Pages).
Requisition by the Examiner Dated Oct. 25, 2021 From the Innovation, Science and Economic Development Canada, Canadian Intellectual Property Office Re. Application No. 2,940,090. (3 Pages).

* cited by examiner

ACTIVE AGENT-CONTAINING MICROCAPSULES

RELATED APPLICATIONS

This application is a National Phase of PCT Patent Application No. PCT/IL2015/050236 having International filing date of Mar. 4, 2015, which claims the benefit of priority under 35 USC § 119 (e) of U.S. Provisional Patent Application No. 61/947,683 filed on Mar. 4, 2014. The contents of the above applications are all incorporated by reference as if fully set forth herein in their entirety.

FIELD AND BACKGROUND OF THE INVENTION

The present invention, in some embodiments thereof, relates to encapsulation and, more particularly, but not exclusively, to newly designed microcapsules, encapsulating active agents such as pharmaceutically, dermatology, and/or cosmetically active agents, and to compositions and/or formulations such as, for example, cosmetic formulations and other topical formulations, containing same.

Compositions for topical applications comprising various colorants or other active substances are known in the art. Previous attempts to use protected colorants in dermal applications were mostly focused towards hydrophobic or solid decorative cosmetics such as make-up, lipstick, blush, and powder products.

U.S. Pat. Nos. 5,320,835 and 5,382,433 disclose "activatable" dormant colored particles or pigments and cosmetic formulations comprising same and further comprising a colored base phase, and colorant entrapping substrate particles dispersed in said base phase. The encapsulated colorants are said to be released into the base phase when mechanical action is applied to the cosmetic formulation, and produce an intense shade in the color of the base phase, whereas the colorant entrapping substrate particles entrap the released colorants and produce a subtle shade in the color of the base phase. The encapsulated pigments are made by a coacervation method.

U.S. Pat. No. 5,380,485 discloses colored cosmetic compositions, comprising particulate fillers coated with polymer that is combined with colorants, and their application in decorative cosmetics.

U.S. patent application having Publication Nos. 2005/0031558 and 2005/0276774 disclose a personal care or cosmetic composition containing microparticles comprising a shatter resistant blend of distinct colorants microencapsulated within a polymer matrix, preferably a cross-linked polymer matrix that does not allow any of the entrapped colorant to be released even under prolonged use. The matrix polymer is preferably transparent or translucent such that the blend of encapsulated colorants provides the coloring of the cosmetic product itself and of the skin upon application of the cosmetic composition. The microparticles disclosed in 2005/0276774 further contain secondary particles (i.e. hydrophobic polymers different from those of the matrix polymer) that are distributed throughout the matrix.

U.S. Pat. No. 4,756,906 discloses decorative cosmetic compositions containing a first colorant and microcapsules containing a solvated second colorant, different from the first colorant. Upon rupture of the microcapsules, the coloration of the encapsulated pigment is added into the composition thereby altering its color characteristics.

U.S. Patent Application Publication No. 2008/81057 discloses compositions comprising at least one encapsulated pigment and at least one skin coloring agent chosen from self-tanning agents and melanogenesis activators. The composition develops a slow, long-term color after application to the skin due to the biological action of the self-tanning agents or the melanogenesis activators, while encapsulated pigments provides immediate coloring of the skin. The pigments are said to be invisible in the composition by virtue of their encapsulation, but are readily released from their capsules and become apparent when applied to the skin through breaking of the capsules by pressure exerted during application of the composition to the skin.

WO 2004/075679 discloses rigid, non-rupturable microcapsules containing a blend of at least two coloring agents and compositions comprising them, which do not change their color upon application onto the skin. The microcapsules are non-rupturable due to the use of cross-linked polymeric matrix comprising polymers that have a glass transition temperature (Tg) higher than 80° C.

U.S. Pat. No. 6,932,984, by the present assignee, discloses single- and double-layer microcapsules and a method for microencapsulation of substances by the solvent removal method using non-chlorinated solvents. The method is based on physical processes which do not cause any change of original physical and/or chemical properties, biological activity, and safety of raw materials during the process.

U.S. Pat. No. 7,838,037, by the present assignee, discloses double-layer and/or triple-layer microcapsules, designed to rupture by a slight mechanical action such as rubbing or pressing on the skin, and thereby immediately release their encapsulated content. These microcapsules are prepared by the solvent removal method using non-chlorinated solvents. This method affords physical stability to the microcapsules, high ability to entrap the active agents, protection of the active agents inside the microcapsules, and prevention of the diffusion of the microencapsulated active agents to the external water phase in a water-based preparation.

WO 2009/138978, by the present assignee, discloses cosmetic compositions for dermal/topical application comprising double-layer, rupturable microcapsules which contain one or more microencapsulated colorants, and active substances. When applied to the skin, such compositions produce an immediate color change effect indicating the delivery to the skin of the active substances contained in said compositions.

SUMMARY OF THE INVENTION

In a cosmetic composition or formulation it is highly desirable to retain an active substance within capsules before application thereof. There is also a need to protect encapsulated active substances from potential detrimental effect caused by other substances, particularly in a combined formulation that comprises active substances in combination with colorants.

The effectiveness of protection or masking by single-layer microencapsulation depends on the chemical structure, molecular weight and physical properties of the microencapsulated ingredient. For some active substances, the known methods of single-layered microencapsulation do not provide an adequate protection from leaking and/or a satisfying masking effect, and hence the use of single-layered microcapsules may result in, for example, coloring of the cosmetic composition before it is applied to the skin, in case a colorant is encapsulated, or is leaching or decomposition of active agents before the composition is applied.

Currently known microcapsules not always provide an adequate protection from leaking and/or a satisfying masking effect of the encapsulated agent. In addition, such microcapsules often exhibit inferior stability in gel and other water-based formulations.

In a search for microcapsules that would not be limited by incompatibility with water-based formulations, and that would exhibit substantial stability in water-based formulations and an improved masking and/or protecting effect and release of the encapsulated agent (e.g., colorant or an active agent as described herein), the present inventors have devised and successfully practiced novel opaque, multi-layered microcapsules.

According to an aspect of some embodiments of the present invention there is provided a multi-layer microcapsule comprising an inner core microcapsule and at least one outer shell enveloping the inner core microcapsule, the inner core microcapsule comprising a core which comprises an active agent, the core being enveloped by a shell comprised of a first wall-forming material, and the at least one outer shell comprising a second wall forming material, a fatty acid salt, and an opaque substance.

According to some of any of the embodiments described herein, the at least one outer shell further comprises a plasticizer.

According to some of any of the embodiments described herein, the plasticizer is selected from the group consisting of triethyl citrate, tricaprylin, trilaurin, tripalmitin, triacetin, acetyltriethyl citrate, paraffin oil, and any combination thereof.

According to some of any of the embodiments described herein, the plasticizer is triethyl citrate.

According to some of any of the embodiments described herein, an amount of the plasticizer ranges from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 3.5% to about 6.0%, or from about 3.5% to about 5.5%, or from about 3.5% to about 5.0%, or is about 4.5% by weight, of the total weight of the microcapsule.

According to some of any of the embodiments described herein, the at least one outer layer further comprises a dispersing agent, capable of dispersing the active agent upon application on the skin.

According to some of any of the embodiments described herein, the dispersing agent is an ester of a fatty acid.

According to some of any of the embodiments described herein, an amount of the dispersing agent ranges s from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 3.5% to about 6.0%, or from about 4% to about 6%, of the total weight of the microcapsule.

According to some of any of the embodiments described herein, the opaque substance is selected from the group consisting of $TiO_2$, zinc oxide, alumina, boron nitride, talc, kaolin, mica and any combination thereof.

According to some of any of the embodiments described herein, an amount of the opaque substance ranges from about 1% to about 90%, or from about 30% to about 90%, or from about 30% to about 60%, by weight of the total weight of the microcapsule.

According to some of any of the embodiments described herein, the opaque substance is $TiO_2$, and wherein an amount of $TiO_2$ ranges from about 10% to about 80%, or from about 30% to about 80%, or from about 30% to about 60%, by weight, of a total weight of the microcapsule.

According to some of any of the embodiments described herein, the fatty acid salt comprises one or more fatty acyls independently selected from the group consisting of stearic acid, arachidic acid, palmitoleic acid, oleic acid, linoleic acid, linolaidic acid, arachidonic acid, myristoleic acid and erucic acid.

According to some of any of the embodiments described herein, the fatty acid salt is selected from the group consisting of magnesium stearate, magnesium oleate, calcium stearate, calcium linoleate, and sodium stearate.

According to some of any of the embodiments described herein, the fatty acid salt is magnesium stearate.

According to some of any of the embodiments described herein, an amount of the fatty acid salt ranges from about 0.05% to about 5%, or from about 0.1% to about 3%, or from about 0.2% to about 3%, or from about 0.5% to about 3%, or from about 0.5% to about 2.0%, or from about 1.0% to about 2.0%, % by weight, of the total weight of the microcapsule.

According to some of any of the embodiments described herein, the multi-layer microcapsule comprises magnesium stearate in an amount within a range of from 1.0% to about 2.0% by weight, TiO2 in an amount within a range of from about 30% to about 75% by weight and a dispersing agent in an amount within a range of from about 4% to about 6% by weight, of the total weight of the microcapsule.

According to some of any of the embodiments described herein, an amount of the inner core microcapsules ranges from about 10% to about 70%, or from about 10% to about 50% by weight of the total weight of the microcapsule.

According to some of any of the embodiments described herein, each of the first and second wall-forming material independently comprises a polymer or copolymer selected from the group consisting of polyacrylate, a polymethacrylate, a cellulose ether, a cellulose ester, and any combination thereof.

According to some of any of the embodiments described herein, the polymer or copolymer is selected from the group consisting of a polyacrylate, a polymethacrylate, acrylate/ammonium methacrylate copolymer, ammonium methacrylate copolymer type B, low molecular weight (about 15,000 Dalton) poly(methyl methacrylate)-co-(methacrylic acid), poly(ethyl acrylate)-co-(methyl methacrylate)-co-(trimethylammmonium-ethyl methacrylate chloride), poly(butyl methacrylate)-co-(2-dimethylaminoethyl methacrylate)-co-(methyl methacrylate), poly(styrene)-co-(maleic anhydride), copolymer of octylacrylamide, cellulose ether, cellulose ester, poly(ethylene glycol)-black-poly(propylene glycol)-black-poly(ethylene glycol), PLA (poly lactic acid), PGA (poly glycolic acid) and PLGA copolymer.

According to some of any of the embodiments described herein, the second wall forming material comprises a polymer or copolymer selected from the group consisting of an acrylate/ammonium methacrylate copolymer, cellulose acetate and a combination thereof.

According to some of any of the embodiments described herein, an amount of the second wall-forming material ranges from about 5% to about 70%, or from about 5% to about 50%, or from about 5% to about 40%, or from about 5% to about 30%, by weight, of the total weight of the microcapsule.

According to some of any of the embodiments described herein, the multi-layer microcapsule comprises the inner core microcapsules in an amount ranging from about 10% to about 50% by weight, the second wall-forming polymer or copolymer in an amount ranging from about 5% to about 30% by weight, magnesium stearate in an amount ranging from about 0.5% to 1% by weight, TiO$_2$ in an amount ranging from about 25% to about 50% by weight and a dispersing agent in an amount ranging from about 1% to about 6%, by weight, of the total weight of the microcapsule.

According to some of any of the embodiments described herein, the multi-layer microcapsule is a double layer microcapsule.

According to some of any of the embodiments described herein, the multi-layer microcapsule is characterized by lightness values (L*) in the range of 60-100 on a lightness scale of an X-Rite measurement system.

According to some of any of the embodiments described herein, the multi-layer microcapsule is stable upon incubation in a gel formulation for at least 3 month at 40° C., while stirring.

According to an aspect of some embodiments of the present invention there is provided a composition comprising a plurality of multi-layer microcapsules, at least a portion of the multi-layer microcapsules comprising a plurality of active agent-containing microcapsules as described herein in any of the respective embodiments and any combination thereof.

According to some of any of the embodiments described herein, the multi-layer microcapsules in the plurality of active agent-containing microcapsules are the same or different.

According to some of any of the embodiments described herein, the plurality of multi-layer microcapsules have a mean size within a range of about 50 µm to about 350 µm.

According to an aspect of some embodiments of the present invention there is provided a process of preparing multi-layer active agent-containing microcapsules, the process comprising:
  (a) contacting a first organic phase comprising a second wall-forming polymer or copolymer, a fatty acid salt, optionally a dispersing agent, and a first partially water-miscible organic solvent with a first aqueous continuous phase saturated with the organic solvent and comprising an emulsifier, to thereby obtain a first multi-component emulsion, wherein either the first organic phase or the first aqueous phase further comprises an opaque substance and/or single-layer microcapsules, each of the single-layer microcapsules comprising a core comprising at least one active agent enveloped by a shell comprised of a first wall-forming material;
  (b) adding to the formed emulsion an amount of water which initiates extraction of the organic solvent from the emulsion, thereby obtaining double-layered microcapsules; and
  (c) optionally repeating steps (a) and (b), using a second, third, and so on, organic phases and aqueous continuous phases, thereby obtaining multi-layered microcapsules.

According to some of any of the embodiments described herein, the process further comprises isolating the microcapsules following step (b).

According to some of any of the embodiments described herein, the process further comprises drying and sifting the microcapsules, to thereby obtain a free flowing powder of the microcapsules.

According to some of any of the embodiments described herein, the wall-forming polymer is acrylate/ammonium methacrylate copolymer, ammonium methacrylate copolymer type B, cellulose ethyl ether, cellulose ethyl ester, or any combination thereof.

According to some of any of the embodiments described herein, the organic solvent is selected from ethyl acetate, ethanol, ethyl formate, or any combination thereof.

According to some of any of the embodiments described herein, the plasticizer is selected from tricaprylin, trilaurin, tripalmitin, triacetin, triethyl citrate, acetyltriethyl citrate, paraffin oil, or any combination thereof.

According to some of any of the embodiments described herein, the opaque substance is selected from TiO$_2$, zinc oxide, alumina, boron nitride, talc, kaolin, mica and any combination thereof.

According to some of any of the embodiments described herein, the wall-forming polymer comprises acrylate/ammonium methacrylate copolymer, ethyl cellulose or a combination thereof; the organic solvent partially miscible with water is ethyl acetate; the dispersing agent is an ester of a fatty acid; the fatty acid salt is magnesium stearate and the opaque substance comprises titanium dioxide.

According to some of any of the embodiments described herein, the multi-layer active agent-containing microcapsules obtained by the process are as defined in any one of the respective embodiments. Namely, the process is for preparing microcapsules as described herein.

According to some of any of the embodiments described herein, the plurality of multi-layer active agent-containing microcapsules described herein are prepared according to the process as described herein.

According to an aspect of some embodiments of the present invention there is provided a cosmetic or cosmeceutical formulation comprising the composition comprising the microcapsules as described herein.

According to some of any of the embodiments described herein, the formulation further comprises a cosmetically or cosmeceutically acceptable carrier.

According to some of any of the embodiments described herein, the formulation is formulated as an oil-in-water emulsion, oil-in-water-in-oil emulsion, water-in-oil emulsion, a water-in-oil-in-water emulsion, an aqueous formulation, an anhydrous formulation, a silicon-based formulation and a powder formulation.

According to some of any of the embodiments described herein, the formulation is in the form of a gel, a powder, cream, foam, lotion, ointment, spray, oil, paste, milk, suspension, aerosol, or mousse.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is an image presenting 3 dishes containing powder that comprises commercial microcapsules encapsulating red, black or yellow colorants (upper dishes) and three dishes containing powders comprising exemplary microcapsules of some embodiments of the invention, encapsulating the same red, black or yellow colorants (lower dishes), as described in Examples 5, 6 and 7, respectively.

Figure 2:
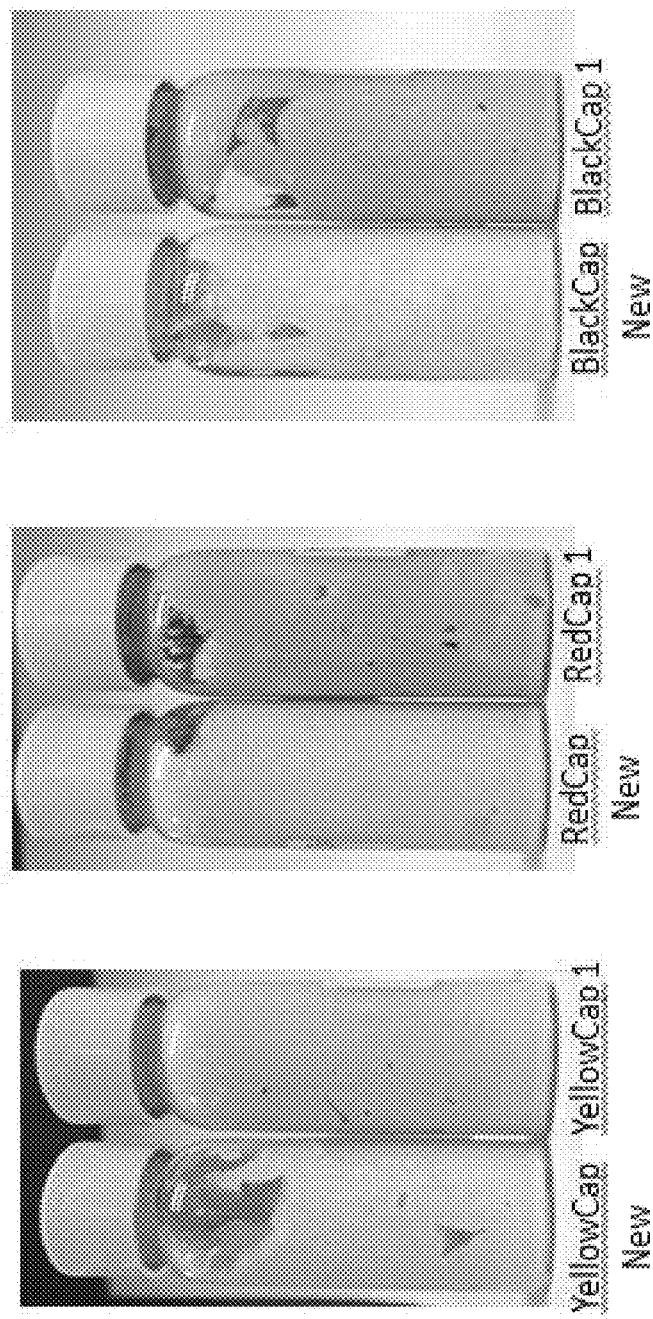

FIG. 2 presents images of three pairs of vials, the left vial in each pair containing a basic body lotion cream comprising exemplary color-containing microcapsules according to some embodiments of the invention (RedCap New, Black Cap New and YellowCap), as described in Examples 8, 9 and 10, and the right vial in each pair containing commercial microcapsules (RedCap 1, Black Cap 1 and YellowCap 1).

Figure 3:
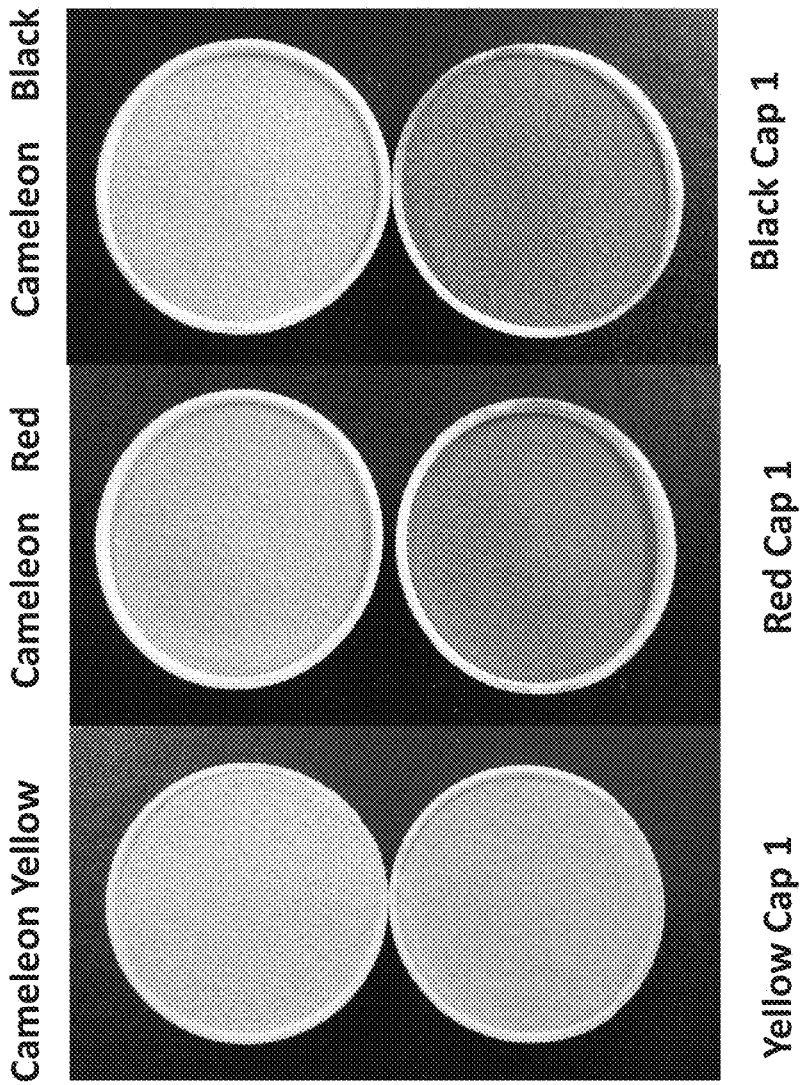

FIG. 3 is an image presenting 3 dishes containing powder that comprises commercial microcapsules encapsulating red, black or yellow colorants (lower dishes) and three dishes containing powders comprising exemplary microcapsules of some embodiments of the invention, encapsulating the same black, red or yellow colorants (upper dishes), as described in Examples 8, 9 and 10.

Figure 4:
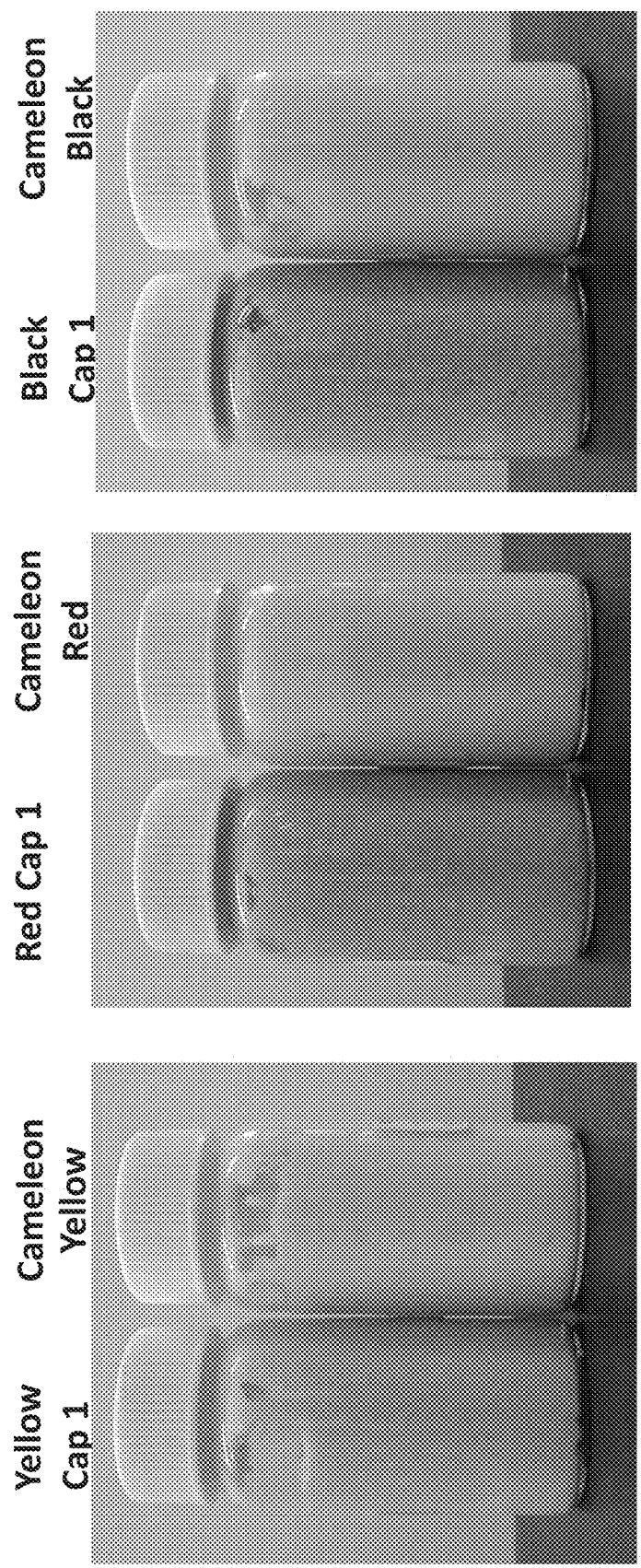

FIG. 4 presents images of three pairs of vials, the right vial in each pair containing a basic body lotion cream comprising exemplary color-containing microcapsules according to some embodiments of the invention (CameleonYellow, CameleonRed, CameleonBlack), and the left vial in each pair containing commercial microcapsules (RedCap 1, Black Cap 1 and YellowCap 1).

Figure 5A:
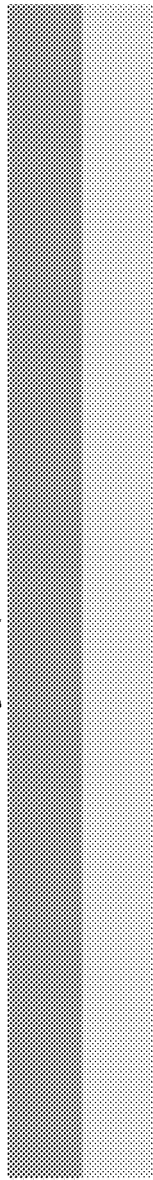
Figure 5B:
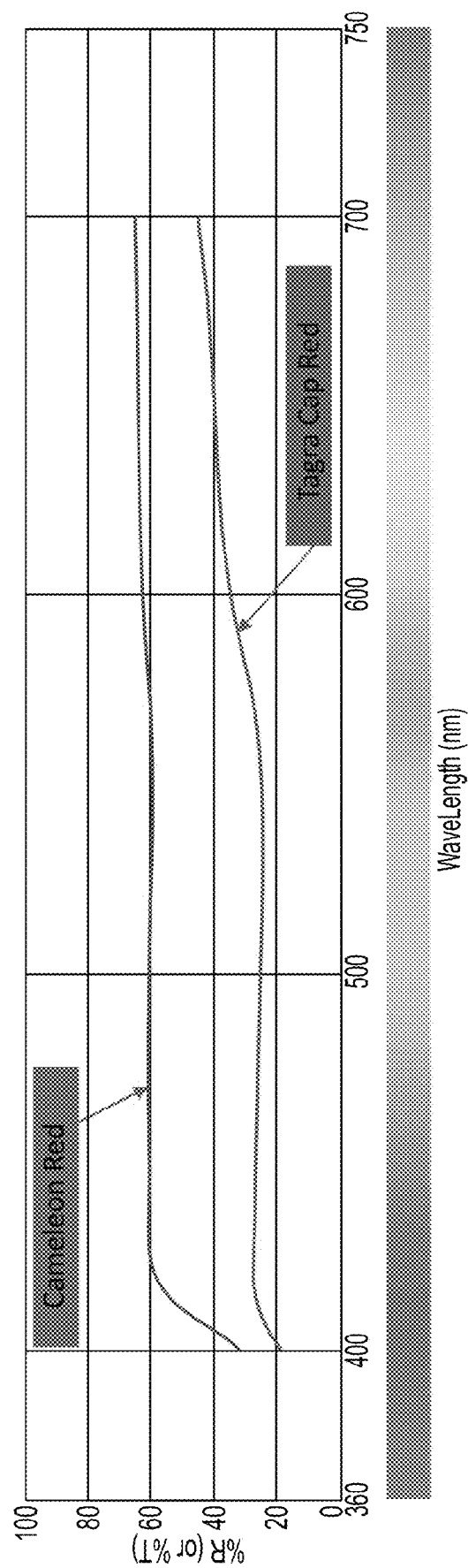

FIGS. 5A-B present data obtained in X-rite measurements for exemplary red colorant-containing microcapsules according to some embodiments of the invention (CameleonRed, Example 8), compared to commercial microcapsules (RedCap 1), and show comparative images taken at the same photographic conditions (FIG. 5A) and comparative graphs showing the reflectance percentage as function of the wavelength (FIG. 5B).

Figure 6A:
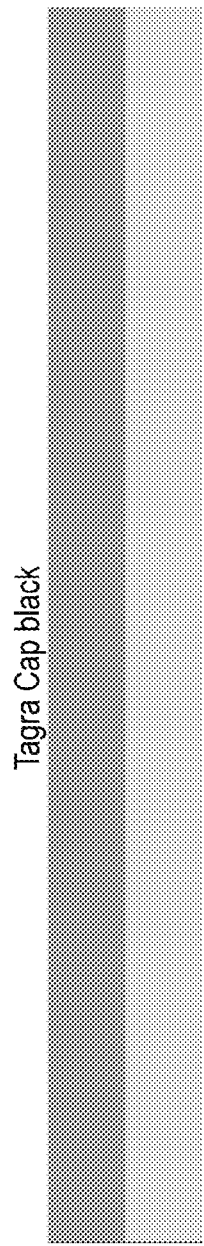
Figure 6B:
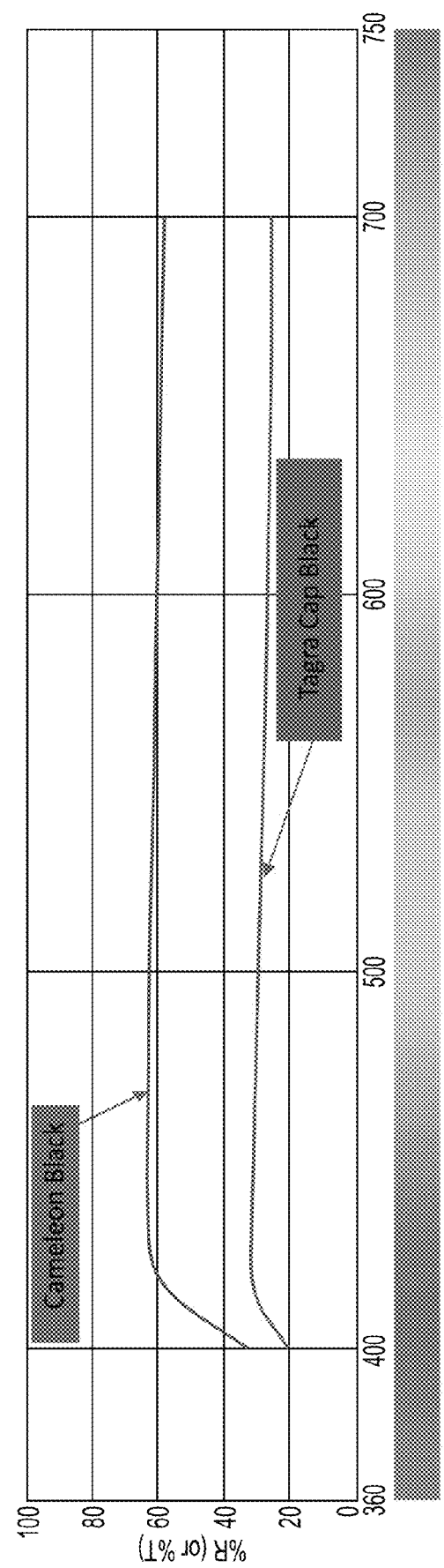

FIGS. 6A-B present data obtained in X-rite measurements for exemplary black colorant-containing microcapsules according to some embodiments of the invention (CameleonBlack, Example 9), compared to commercial microcapsules (BlackCap 1), and show comparative images taken at the same photographic conditions (FIG. 6A) and comparative graphs showing the reflectance percentage as function of the wavelength (FIG. 6B).

Figure 7A:
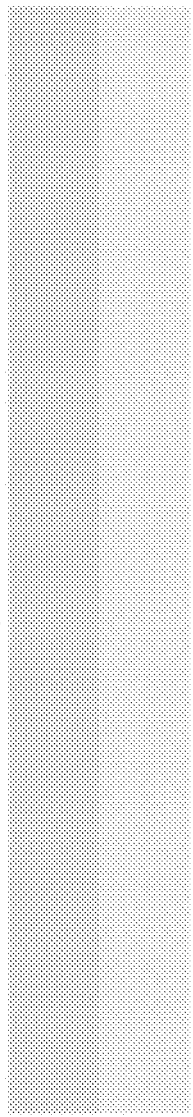
Figure 7B:
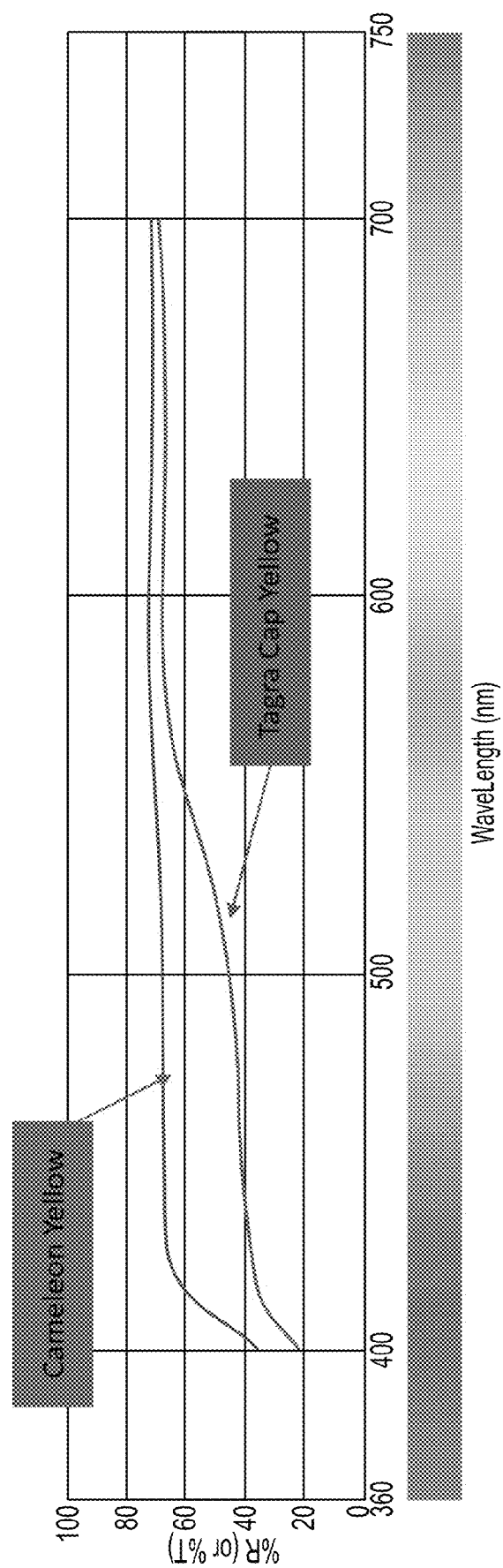

FIGS. 7A-B present data obtained in X-rite measurements for exemplary yellow colorant-containing microcapsules according to some embodiments of the invention (CameleonYellow, Example 10), compared to commercial microcapsules (YellowCap 1), and show comparative images taken at the same photographic conditions (FIG. 7A) and comparative graphs showing the reflectance percentage as function of the wavelength (FIG. 7B).

DESCRIPTION OF SPECIFIC EMBODIMENTS OF THE INVENTION

The present invention, in some embodiments thereof, relates to encapsulation and, more particularly, but not exclusively, to newly designed microcapsules, encapsulating active agents such as pharmaceutically, dermatology, and/or cosmetically active agents, and to compositions and/or formulations such as, for example, cosmetic formulations and other topical formulations, containing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for skin care, particularly cosmetic, products containing encapsulated active agents, that provide improved properties of the capsules such as improved stability, including stability in aqueous-based formulations, and improved masking and release of active agents, the present inventors have devised and successfully practiced novel multi-layered microcapsules.

The present inventors have modified the known solvent removal microencapsulation technique for encapsulating active agents within opaque, multi-layer microcapsules that, on one hand, exhibited unexpected stability when compounded in industrial processes and when maintained in aqueous environment, significantly enhanced masking or protection of the agents encapsulated therein and provided an adequate protection from a leaching effect within the cosmetic formulation and, on the other hand, were readily rupturable only by applying a mechanical pressure/shear force such as rubbing action of a formulation into skin, thereby releasing the encapsulated agent.

The modified solvent removal method is based on physical processes which do not cause any change of original physical and/or chemical properties and safety of raw materials during the process. This method affords physical stability of the microcapsules, high ability to entrap the active agents, protection of the active agents inside the microcapsules, and prevention of the diffusion of the microencapsulated agents to the external medium in both oil-based and water-based preparations (before application).

Thus, the present inventors have designed and successfully practiced a novel methodology for obtaining stable formulations, effectively concealing the microencapsulated agent contained therein, and exhibiting exceptional long term stability before application, smooth and pleasant spread of the microcapsules upon application and immediate release of the encapsulated agent by mere rubbing the formulations on the skin.

For example, the present inventors have demonstrated that basic body lotion formulations, as well as pressed powders, comprising color-containing microcapsules prepared using the methodology as described herein, were significantly lighter and brighter in color compared to corresponding formulations comprising colorant-containing microcapsules made by a solvent removal method as previously described. Moreover, the present inventors have demonstrated that the color-containing microcapsules provided herein were stable in gel formulations up to at last three months when kept at 40° C. under continuous stirring.

Microcapsules provided by the present embodiments are consisted of particles (e.g., generally spherical particles), which are generally closed structures containing an encapsulated (enveloped, entrapped) agent or a mixture of agents. The particles generally have a core-shell structural feature, namely it is comprised of at least two polymeric shells and a core that comprises an active agent or may be consisted of the active agent, enveloped by these shells. More particularly, the multi-layer microcapsule is featured as comprising an inner core microcapsule comprising a core which comprises an active agent, being enveloped by a shell comprised of a first wall-forming material, and at least one additional outer shell comprised of a second wall forming material enveloping said inner core microcapsule (comprising the active agent-containing core and a shell of a first wall-forming material).

Each shell in the multi-layered microcapsules is typically and independently applied as a wall-forming material (e.g., a first, second, third and so forth wall-forming materials forming the first, second, third, and so forth, outer shells, respectively), and serves as a membrane for the encapsulated substance. One or more of the outer shells in the colorant-containing microcapsules provided by the present embodiments is opaque by virtue of an opaque substance comprised therein, and further contains a fatty acid salt.

The outer shells may further contain a plasticizer to control its hardness and/or a dispersing agent that facilitates the smooth spread of active agents on the skin, and are designed such that the microcapsules are rupturable upon rubbing or pressing on the skin.

The microcapsules of the present embodiments, among other uses, are suitable for inclusion in topical, e.g., cosmetic, cosmeceutical and pharmaceutical (e.g., dermatological) applications. While applied to the skin, the microcapsules are capable of being ruptured upon application of shear forces such as rubbing and pressing on the skin, but they remain intact in the formulation itself before application, and exhibit exceptional stability in water-based formulations as well as in other formulations. The microcapsules are hard enough to avoid destruction of the shells and realization of the content during production processes such as isolation, drying, sieving, etc.

The Microcapsules:

According to an aspect of some embodiments of the present invention there is provided a multi-layer microcapsule comprising an inner core microcapsule comprising a core which comprises an active agent as described herein and being enveloped by a first shell comprised of a first wall-forming material; and at least one outer shell comprised of a second wall forming material enveloping the inner core microcapsule. Such multi-layer microcapsules are also referred to herein as active agent-containing microcapsules.

A core of a multi-layer microcapsule as described herein comprises a core-shell microcapsule, which is referred to herein as an inner core microcapsule, or an inner core-shell microcapsule. The inner core microcapsule comprises a core, which comprises, or consists of, an active agent or a mixture of active agents, as described herein, and a shell enveloping the core, which is referred to herein as a first shell or a first outer shell. The shell of the inner core microcapsule comprises a first wall-forming polymer, as described herein, and may optionally further comprise a plasticizer, as described herein. The inner core-shell microcapsule is enveloped by a second outer shell, and optionally by third, fourth and so on, outer shells, each enveloping the preceding shell.

In some embodiments, a multi-layer microcapsule as described herein comprises one outer shell enveloping an inner core-shell microcapsule, thereby forming a double-layer (or double-layered) microcapsule, or can comprise two outer shells, thereby forming three-layer (or three-layered), or three or more outer shells, collectively referred to as multi-layer (or multi-layered) microcapsules. Double-layer microcapsules comprise one outer shell enveloping the inner core microcapsules, whereas triple-layer microcapsules comprise two sequential outer shells enveloping the inner core microcapsules.

In some embodiments, the multi-layer microcapsules containing the active agents as described herein are prepared by a modified solvent removal method, as described in the Examples section that follows.

In some embodiments, a mean size of the microcapsules as described herein is within a range of from about 50 µm to about 350 µm, or from about 50 µm to about 150 µm, including any intermediate value or subranges therebetween.

In some of any of the embodiments described herein, one or more of the outer shells comprises, in addition to the wall-forming material, a fatty acid salt, and an opaque substance, as described herein.

According to some of any of the embodiments of the present invention, one or more of the encapsulated agents is a color agent, as described herein, and the multi-layered microcapsules are characterized by a color significantly lighter when compared to previously described microcapsules, which differ from the microcapsules provided herein by the absence of a fatty acid salt in their wall-forming material and/or by the preparation process thereof.

According to some embodiments of the present invention, a lightness of such microcapsules is measured using the X-Rite measurement technique, and is expressed by L*a*b* values, or, alternatively, by comparative DL* values on the lightness scale (L*), as the lightness difference compared to similar microcapsules, containing the same colorant, but not containing fatty acid salts, and which are prepared using a previously described solvent removal method.

According to some embodiments of the present invention, a lightness of the microcapsules is measured using the X-Rite measurement technique, is expressed by the lightness scale (L*), and is higher than 60, higher than 70, higher than 80 or higher than 90. In some embodiments the lightness is in the ranges of 60-100 in the lightness scale L*.

In exemplary embodiments, the lightness of the microcapsules of some exemplary embodiments, containing red, yellow or black colorants was measured using the X-Rite measurement technique, and it was observed, as described, for example, in Example 13 herein, that the lightness values on the lightness scale (L*) were higher by 4-25 (as reflected by the measured DL*s values, relative to the lightness of exemplary similar commercial microcapsules that contained the same colorants, but did not contain fatty acid salts and were prepared using a different solvent removal method.

In further exemplary embodiments, described in Example 13 and presented in FIGS. 1-4, a visual, qualitative comparative measurements of color lightness of formulations containing either microcapsules according to exemplary embodiments of the invention or commercial microcapsules as described herein, both containing the same colorants, have been made. It is shown that powders (FIGS. 1 and 3) and basic body lotions (FIGS. 2 and 4) that comprised the microcapsules of exemplary embodiments of the present invention were significantly lighter and brighter compared to powders and lotions that contained commercial microcapsules encapsulating the same black, red or yellow colorants.

The microcapsules of these exemplary embodiments comprise $TiO_2$ in their outer wall-forming material, and it is assumed that the $TiO_2$ is uniformly enveloping the polymeric shell (first outer shell) of the inner core microcapsule and that, without being bound by any particular theory, this accounts for the lighter color.

Without being bound by any particular theory, it is assumed that the use of a fatty acid salt accounts for enhanced adhesion of the opaque substance and optionally of the outer polymeric shells to the inner core microcapsule, further accounting for the lighter color and/or improved stability of the microcapsules.

The lighter color exhibited by such microcapsules demonstrates as improved masking/protecting effect of the encapsulated agent.

According to some of any of the embodiments of the invention, a multi-layer microcapsule as described herein is rupturable or breakable when applied to the skin; that is, a microcapsule as described herein remains intact in the formulation, including water-based formulation, and during industrial processes, but readily breaks when pressed of rubbed on the skin. The non-breakability of the microcapsules before topical application thereof is routinely assessed by monitoring (e.g., using a light microscope) the ability of the microcapsules in a basic cream or lotion to sustain their size and shape when subjected to low shear mixing at e.g., 40-600 (or 80-100) rpm for 5-10 minutes at room temperature and at 40° C. A change of less than 10% in the microcapsule size is indicative of the non-breakability of the microcapsules upon routine industrial processes.

The multi-layer microcapsules provided herein have shown exceptional stability in water-based formulations in general and in gel formulation in particular.

In exemplary embodiments, for example as described in Example 14 herein, the durability of the multi-layer microcapsules provided in exemplary embodiments of the present invention in gel formulation was tested. It was observed that a carbomer gel formulation containing about 3% by weight of exemplary microcapsules of the present embodiments containing red, yellow or black was incubated at 40° C. for at least 3 months, under continuous stirring, yet the color of the gel was not changed, namely no color leaked from the microcapsules to the gel, and at least 90% of the microcapsules maintained their shape and size throughout the long incubation. This is indicative of the stability of the active agent-containing microcapsules.

The Wall Forming Material:

The wall-forming material forms the shells of the multi-layer microcapsules of the present embodiments, and serves as a membrane for the encapsulated substance (e.g., colorant and/or active agent). According to embodiments of the present invention, each of the wall forming materials forming the shells comprises a wall-forming polymer or co-polymer. In some of any of the embodiments of the present invention, one or more of the outer shells further comprises an opaque substance and a fatty acid salt, and may optionally further comprise a plasticizer and/or a dispersing agent.

The phrase "wall-forming polymer", which is also referred to herein as "wall-forming polymeric material" refers to a polymeric material (e.g., a polymer or copolymer) or a combination of two or more different polymeric materials, as defined herein, which form a component of the external wall or layer or shell of the microcapsules. The term "polymer shell" refers to a polymer layer comprised of the wall-forming polymer(s).

In some embodiments, the wall-forming polymer is selected so as to sustain shear forces applied while being compounded in industrial processes, but, nevertheless, so as to provide microcapsule which are rupturable when applied (e.g., rubbed or pressed) on the skin.

In some embodiments, each of the wall-forming polymeric materials independently comprises a polymer containing a sufficient amount of functional groups which are capable of forming hydrogen bonds.

In some embodiments, one or more, or each, of the polymeric materials forming the two or more shells comprises hydrogen bond-forming functional groups featuring 4-40 weight percents of total polymer weight. Hydrogen bond-forming functional groups include, but are not limited to, functional groups which comprise one or more electron-donating atom(s) such as oxygen, sulfur and/or nitrogen.

In some embodiments, the hydrogen bond-forming groups include carboxylic acid, carboxylate, hydroxy, or any combination thereof.

In some embodiments, one or more, or each, of the wall-forming polymeric materials forming the two or more shells comprises a polyacrylate, a polymethacrylate, a cellulose ether or ester, or any combination thereof.

Exemplary wall-forming polymeric materials include, but are not limited to, polyacrylate, a polymethacrylate, low molecular weight poly(methyl methacrylate)-co-(methacrylic acid) (e.g., 1:0.16), poly(ethyl acrylate)-co-(methyl methacrylate)-co-(trimethylammmonium-ethyl methacrylate chloride) (e.g., 1:2:0.1) (also known as Eudragit® RSPO), poly(butyl methacrylate)-co-(2-dimethylaminoethyl methacrylate)-co-(methyl methacrylate) (e.g., 1:2:1), poly(styrene)-co-(maleic anhydride), copolymer of octylacrylamide, cellulose ethers, cellulose esters, poly(ethylene glycol)-block-poly(propylene glycol)-block-poly(ethylene glycol), PLA (poly(lactic acid), PGA (poly(glycolide), PLGA (poly(lactide)-co-poly(glycolide) or any combination thereof.

Any combination of polymers and co-polymers as described herein is contemplated for a wall-forming material, as described herein.

In some embodiments, the wall-forming polymeric material of at least one of the outer shells comprises a cellulose ether or ester such as, but not limited to, methyl cellulose, ethyl cellulose, hydroxypropyl methyl cellulose, hydroxypropyl cellulose, cellulose acetate, cellulose acetate phthalate, cellulose acetate butyrate and hydroxypropyl methyl cellulose acetate phthalate. When a cellulose ether or ester is used in the polymeric material, it preferably contains about 4-20% hydroxyl groups which are free to form hydrogen bonds (e.g., hydroxyl groups which are not alkylated or acylated).

In some of any of the embodiments described herein, the first outer shell, of the inner core microcapsules comprises a wall-forming material as described in U.S. Pat. No. 6,932,984, which is incorporated by reference as if fully set forth herein.

In some of any of the embodiments described herein, the wall-forming material of one or more of the second, third, and so forth outer shells, comprises an acrylate/ammonium methacrylate copolymer such as, for example, Eudragit® RSPO. In some of any of the other embodiments of the present invention, the wall-forming material of one or more of the second, third, and so forth outer shells, comprises a combination of the above-mentioned polymers such as, but not limited to, combinations of acrylate/ammonium methacrylate copolymer (e.g., Eudragit® RSPO) with either poly(methyl methacrylate)-co-(methacrylic acid) or cellulose acetate.

In some embodiments, the wall-forming material of one or more of the second, third, and so forth outer shells, comprises cellulose ester such as cellulose acetate. In some of any of the other embodiments of the present invention, the wall-forming material of one or more of the second, third, and so forth outer shells, comprises a combination of cellulose acetate and acrylate/ammonium methacrylate copolymer (e.g., Eudragit® RSPO) or poly(methyl methacrylate)-co-(methacrylic acid).

When two polymeric materials are used as a wall-forming material, a weight ratio therebetween can range from 10:1 to 1:1, and can be, for example, 5:1, 4:1, 3:1, 2:1, or 3:2, including any intermediate values and subranges therebetween.

The wall-forming material in each of the outer shells in the microcapsules described herein (e.g., a first wall-forming material of the inner microcapsule, a second wall-forming material of a first outer shell enveloping the inner microcapsule, and optionally a third wall-forming material of a second outer shell enveloping the first outer shell, and so forth) can be the same or different.

In some embodiments, in double-layer microcapsules, the wall forming material of the first and second outer shells is different. In some of these embodiments, the second wall-forming material comprises cellulose acetate, acrylate/ammonium methacrylate copolymer (e.g., Eudragit® RSPO) or a combination thereof.

The total amount (weight/weight) of the wall-forming polymeric material(s) of the outer shells (excluding the inner capsules) in the total microcapsule weight can be within a range selected from about 5% to about 70%, from about 5% to about 50%, from about 5% to about 40%, or from about 5% to about 30%, or from about 8% to about 21%, by weight, including any subranges and any intermediate values therebetween.

In embodiments where the wall forming material comprises cellulose acetate, an amount of the wall-forming polymeric material(s) of the outer shells (excluding the inner capsules) of the total microcapsule weight can be within a range of from 5% to 20% or from 5% to 20% by weight.

An Opaque Substance:

The shells of the microcapsules can independently be opaque, semi-opaque or non-opaque (transparent). In some embodiments, at least one of the outer shells, for example, the most outer shell, is opaque.

In some embodiments of the present invention, opacity of the outer shell of the multi-layer microcapsules is obtained by an opaque substance.

As used herein, an "opaque substance" is a substance which is non-transparent and blocks at least 70% of the light passing therethrough.

Thus, opaque outer shell blocks 70% to 100% of the light. Semi-opaque outer shell blocks up to 50% of the light. Non-opaque or transparent outer shell blocks no more than 30% of the light passing therethrough.

The terms "opacity" and "opaque" refer to herein to UV-vis light, such as, for example, daylight.

Exemplary opaque substances include, but are not limited to, $TiO_2$, zinc oxide, alumina, boron nitride, talc, mica and any combination thereof.

The total amount of opaque substances in at least one outer shell is within a range of from about 1% to about 90%, or from about 10% to about 90%, or from about 30% to about 90%, or from about 30% to about 80%, or from about 30% to about 60%, by weight, of the total weight of the microcapsule, including any subranges and any intermediate values therebetween.

In some of any of the embodiments described herein, the opaque substance is, or comprises, $TiO_2$, and in some embodiments, an amount of $TiO_2$ is within a range of from about 10% to about 85%, or from about 30% to about 80%, or from about 30% to about 75%, or from about 30% to about 60%, by weight, of the total weight of the microcapsule, including any subranges and any intermediate values therebetween.

In some of any of the embodiments described herein, the opaque substance comprises $TiO_2$ in combination with boron nitride.

A Fatty Acid Salt:

A technical feature of the multi-layer microcapsules of the present embodiments, which is assumed to account for their ability to sustain opacity and remain stable in water-based environment, is that one or more of the outer shells comprises a fatty acid salt.

In some of any of the embodiments described herein, the outer shell which comprises an opaque substance as described herein in any one of the respective embodiments further comprises a fatty acid salt as described herein in any one of the respective embodiments.

A fatty acid salt comprises a long hydrophobic hydrocarbon chain (e.g., of 4 to 30 carbon atoms in length) carboxylate anion (a fatty acyl) and a cation, as depicted in the following formula:

$$(R\text{—}C(\!=\!O)\text{—}O^-)_n M^{(n+)}$$

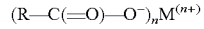

wherein R is a substituted or unsubstituted, liner or branched hydrocarbon chain of 4 to 30 carbon atoms, M+ is a cation, preferably a metal cation, and n is an integer representing the number of fatty acyls that interact with the cation, and also represents the charge number of the cation (e.g., 1, 2, 3, etc.).

The fatty acids salts that are used in some of any of the embodiments of the present invention may contain 1 to 3 fatty acyl chains, each chain, independently, comprising 4 to 30 or 8 to 24 carbon atoms (C8-C24) in length. Thus, the fatty acid salt can be a salt of a monovalent, divalent or trivalent metal ion or a salt of an organic cation.

A monovalent metal ion can be, for example, $Na^+$, $K^+$, $Cs^+$, $Li^+$; a divalent metal ion is selected from $Mg^{2+}$, $Ca^{2+}$, Fe(II), $Co^{2+}$, $Ni^{2+}$, $Cu^{2+}$, $Mn^{2+}$, $Cd^{2+}$, $Sr^{2+}$ or $Zn^{2+}$; a trivalent metal ion can be, for example, Fe(III), $La^{3+}$, $Eu^{3+}$ or $Gd^{3+}$; an organic cation can be, for example, ammonium, sulfonium, phosphonium or arsonium.

The fatty acyl can be derived from fatty acids such as, but not limited to, stearic acid, arachidic acid, palmitoleic acid, oleic acid, linoleic acid, linolaidic acid, arachidonic acid, myristoleic acid and erucic acid. Other fatty acids are also contemplated.

Without being bound by any particular theory, it is assumed that the hydrocarbon chain minimizes contact with aqueous environment, while the ionic cation head forms ionic interactions with water molecules and anionic substances. Thus, in some embodiments of the process of the preparation of the multi-layer microcapsules of the invention, when the inner core microcapsules and the opaque substance are brought in contact with a salt of a fatty acid and a wall-forming polymer, the long hydrophobic chains of the fatty acid carboxylate spontaneously wrap themselves around the hydrophobic outer shell of the inner core microcapsules while pointing their ionic heads towards the aqueous surrounding, thereby either being solvated by water molecules, or, most often, attracting anionic compounds or compounds with partially-negative charge. Thus, the cation of the fatty acid salts most probably attracts the particles of an opaque substance and optionally the free carboxylic and/or hydroxyl groups of the wall-forming polymer dispersed in the aqueous emulsion, resulting in a better adhesion of both the opaque substance and the polymeric material to the outer layer of the inner core microcapsules and hence provide efficient protecting or masking of the active agent in the inner core microcapsules, while producing multi-layer microcapsules.

Fatty acid salts may be used in the preparation of single-layer microcapsules while being added to the organic phase together with the encapsulated material, and the wall-forming polymer, with or without the opaque substance. Upon contacting the organic phase with an aqueous phase, the fatty chains will spontaneously wrap around the encapsulated substance and their polar/ionic heads will interact with the oppositely charged opaque substance as well as with oppositely charged groups on the polymer, thereby enhancing the formation of an opaque polymeric envelope surrounding a core comprising the encapsulated material.

Exemplary fatty acid salts include, but are not limited to, magnesium stearate, magnesium oleate, calcium stearate, calcium linoleate, sodium stearate, magnesium arachidonate, magnesium palmitate, magnesium linoleate, calcium arachidonate, calcium myristoleate, sodium linoleate, calcium linoleate, sodium stearate, potassium stearate, sodium laurate, sodium myristate, sodium palmitate, potassium laurate, potassium myristate, potassium palmitate, calcium laurate, calcium myristate, calcium palmitate, zinc laurate, zinc myristate, zinc palmitate, zinc stearate, magnesium laurate, and magnesium myristate.

In some embodiments, the fatty acid salt is magnesium stearate.

The fatty acid salt is usually in an amount within a range of from about 0.05% to about 5%, or from about 0.1% to about 45%, or from about 0.2% to about 4%, or from about 0.5% to about 4%, or from about 0.5% to about 3.0%, or from about 0.75% to about 3.0%, or from about 1.0% to about 3.0%, or from about 1.0% to about 2.0%, or is about 1.0% or about 2.0%, by weight, of the total microcapsule's weight, including any subranges and any intermediate values therebetween.

A Dispersing Agent and/or Plasticizer:

In some embodiments, the one or more of the outer shells of the multi-layer microcapsule comprises a dispersing agent, preferably a lower alkyl fatty acid ester such as, but not limited to, isopropyl myristate, isopropyl butyryl myristate, propylene glycol stearate, butylene glycol cocoate, hydrogenated lecithin and jojoba oil.

In some embodiments, the dispersing agent is isopropyl myristate (IPM), propylene glycol stearate, or a combination thereof. It was observed that when a dispersing agent such as IPM or propylene glycol stearate was included in the outer shell of double-layered microcapsules, softer, and more readily spreadable, microcapsules were obtained. It is assumed that when the microcapsules break, the encapsulated agent is released and coated with the oily dispersing agent, which thereby accounts for smoother and a uniform spread of the active agent on the skin. Such fatty agents can be considered as acting both as a plasticizer and a dispersing agent.

The amount of a dispersing agent is usually within a range of from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 4.0% to about 6.0%, by weight, of the total weight of the multilayer microcapsule, including any subranges and any intermediate values therebetween.

In some embodiments of any of the embodiments of the present invention, one or more of the outer shells (e.g., a first and/or second outer shell(s) in a double-layer microcapsule) further comprises a plasticizer.

Herein and in the art, a "plasticizer" describes a substance which increases the plasticity or fluidity of a composition. In the context of the present embodiments, a plasticizer is added to the wall-forming material in order to control the physical properties and level of elasticity of the microcapsule's outer shells.

Exemplary plasticizers include, but are not limited to, triethyl citrate, tricaprylin, trilaurin, tripalmitin, triacetin, acetyltriethyl citrate, paraffin oil, and any combination thereof. In exemplary embodiments, the plasticizer is triethyl citrate.

The amount of the plasticizer in can be within a range of from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 3.5% to about 6.0%, or from about 3.5% to about 5.5%, or from about 3.5% to about 5.0%, or is about 4.5% by weight, of the total weight of the microcapsule, including any subranges and any intermediate values therebetween.

The Active Agent:

The active agent (also referred to herein as active ingredient or active substance) to be encapsulated may be an agent having biological activity (e.g., a pharmaceutically or dermatologically active agent, a cosmetic agent), an odor agent such as fragrances, a color agent such as a pigment and colorant and volatile natural and synthetic compounds.

The agent having biological activity may be selected from vitamins, natural extracts, individual compounds isolated from natural sources or prepared synthetically, essential oils, and pharmaceutically active agents for topical or transdermal applications, as described herein.

Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like), and vitamins D, E, F, K, P, or mixtures thereof.

In some embodiments, the vitamin is vitamin A, either in its free form as Retinol or in its ester form as Retinol Palmitate. The most useable form of the vitamin is Retinol, the active form in the body. Retinol is an anti-oxidant vitamin used as nutritional factor and also as an active ingredient of topical/dental products. The activity of one IU (International Unit) of vitamin $A_1$ (equivalent to a USP unit) is 0.3 μg of all-trans Retinol. Retinol can be used for topical treatment of *Ichthyosis vulgaris* (an inherited skin disorder characterized by cornification of the skin) and common acne, and in anti-aging and rejuvenation formulations. However, Retinol (an unsaturated alcohol) is a small and unstable molecule and undergoes chemical degradation/oxidation due to its high potential for chemical reactions with other molecules and should be stabilized before using it as an active ingredient in compositions. In order to enjoy the beneficial effects of Retinol and meet the shelf-life needed for topical/dental compositions, this active principle should be protected from oxidation. Encapsulation of Retinol by the single- or double-layered encapsulation method of the invention with an appropriate shell provides an effective solution for its stabilization and protection. The Retinol microcapsules of the invention are highly compatible with all types of topical/dental formulations and can be used in various applications including, without limiting, dental products, anti-aging products (creams, lotions, serums and masks), skin regeneration formulations, nourishing and moisturizing creams and anti-acne products.

In some embodiments, the vitamin is vitamin C (ascorbic acid), used in recent years as an active ingredient of cosmetics. Due to its antioxidant properties it is considered to confer both antioxidant and photoprotection to skin against free radical attack and UV ray damage. However, Vitamin C is easily oxidized and, upon storage, exposure to light, oxygen, moisture and/or high temperature, undergoes rapid degradation. It is unstable in aqueous solution, even under neutral pH and at room temperature. The microencapsulation of Vitamin C according to the present invention permits its use as active ingredient in cosmetic composition for use as moisturizing cream, anti-aging cream, anti-wrinkle cream, sunscreen cream, and for stimulating collagen production.

In some embodiments, the vitamin is vitamin E, preferably as α-tocopherol. Tocopherols (Vitamin E) are well-known for their antioxidant properties making vitamin E one of the most widely consumed vitamins. However, vitamin E in its ester form (e.g., tocopherol acetate) is only effective as antioxidant to the formulation, but not to the skin. To be effective as antioxidant to the skin, a tocopherol has to be used, but it is inherently unstable. The microcapsules of the invention preferably contain stable 25±1% α-tocopherol, and can be used in various types of cosmetic formulations such as sunscreen products, shampoos, conditioners, hair gels, liquid make-up and make-up tissue remover, and release about 95-97% of Vitamin E directly onto the skin/scalp upon application.

In some embodiments, the vitamin is vitamin F, a mixture of unsaturated fatty acids essential for skin health and functionality, also known as Essential Fatty Acids (EFA; linoleic acid and alpha-linolenic acid.). Vitamin F oxidizes rapidly when incorporated in cosmetic formulation. The microencapsulation according to the invention offers a stable, active and odorless system of Vitamin F suitable for incorporation into moisturizing creams, anti-aging agents and anti-dryness serums. The microcapsules of the invention preferably contain stable 14±0.2% linolenic and linoleic free fatty acids α-tocopherol.

In some embodiments, the vitamin is Rutin (quercetin-3-rutinoside or vitamin P1), one of the most active natural flavonoids, highly effective as an antioxidant and free radical scavenger and in the treatment of cellulite due to its ability to control cross-linking of collagen synthesis. Rutin is widely applied in dermatological and cosmetic products due to its beneficial effects on the appearance of healthy skin and is well known for its potent antioxidant and anti-inflammatory properties and ability to strengthen and modulate the permeability of the walls of the blood vessels including capillaries. However, when incorporated into cosmetic formulations in its non-encapsulated form, Rutin tends to react with other ingredients and oxidizes quickly, resulting in change of the original color of the formulation and loss of its original biological activity. In order to maintain its potent biological activity and prevent its oxidation in cosmetic formulations, Rutin should be stabilized. The Rutin microcapsules of the present invention, developed specifically for topical application in order to stabilize the Rutin, preferably contain a high concentration (about 7%) of pure Rutin Hydrate from plant source.

In some embodiments, the active ingredient having biological activity is a natural extract. In cosmetics, a natural extract is assumed to mean ingredients of botanical origin. To be truly natural it must be extracted from the relevant part of the plant without undergoing any significant chemical change.

This definition includes plant oils. Any herbal extract or plant oil used for topical application, for example in the cosmetic industry, can be used according to the invention, but preferred herbal extracts and plant oils for encapsulation according to the invention include Licorice root extract, Grape Seed extract, Borage oil, Evening Primrose oil and *Hippophae* oil.

In some embodiments, the natural extract is Grape Seed extract (GSE). GSE contains a high content of proanthocyanidins (also known as Oligomeric Proanthocyanidin Complexes or OPCs), a class of nutrients that belong to the flavonoid family and are potent antioxidants and free radical scavengers, reducing the harmful effects of UV radiation. In topical use, a great advantage of OPCs is a substantial increase in blood circulation at the sub-epitopical level and an improvement of intracellular membrane exchange of micronutrients. The proanthocyanidins (OPCs), however, are not stable and oxidize rapidly due to temperature and light influence or cross-reactions with other ingredients of topical formulation. The brown color developed in the final product is a result of OPCs oxidation. Encapsulation of GSE according to the present invention prevents oxidative degradation and brown color development, since the polymeric microcapsule walls prevent interaction of Grape Seed extract with other ingredients of the formulation, as well as guarantees the maximum release of OPCs from capsules on the skin upon application with maximum biological affect. The microcapsules of the present invention contain natural GSE rich m proanthocyanidins (min. 95% OPC), preferably about 6% GSE, have a uniform spherical shape with an average size of about 40 microns, and increase the stability and shelf-life of the OPCs, maintain its original activity, and prevents the oxidation and color development in the cosmetic formulation. They are thus indicated as an active ingredient for incorporation in anti-aging creams, in after-sun creams for reduction of skin erythema, in moisturizing and revitalizing products, and in facial sunscreens for prevention of UV-induced lipid oxidation in skin.

In some embodiments, the natural extract is Licorice root extract rich in Glabridin, a flavanoid known for its beneficial effects on the skin due to its anti-inflammatory and antioxidant properties. In addition, Glabridin has whitening/lightening and anti-spot properties, probably due to inhibition of tyrosinase and melanin synthesis. However, this extract tends to oxidize easily, resulting in a loss of Glabridin's original whitening activity. Moreover, Glabridin, as a flavanoid, is sensitive to pH changes and this factor is the reason for extreme instability of Glabridin in topical formulations, resulting in loss of its original activity and in the development of a dark brown color in formulations. The microcapsules of the present invention contain Licorice root extract rich in Glabridin. The product is standardized by a content of 4% Glabridin, which is protected by the microcapsules. These microcapsules provide stable lightening whitening agent, prevent oxidation of the Glabridin, thereby guaranteeing original activity of Glabridin and providing a longer shelf life of the end product; prevent development of brown color in formulations; are highly stable in a wide pH range; are freely dispersible in all types of cosmetic formulations; and provide a unique control release of the extract only upon application onto the skin. The Licorice Extract microcapsules of the invention are, therefore, indicated as an active ingredient in whitening creams and lotions, age-defying creams and serums, anti-spots treatment formulations and lightening hand creams.

In some embodiments, the natural extract is Borage oil, rich in essential fatty acids such as linoleic acid, gamma-linolenic acid (GLA), oleic acid and others, in their triglyceride form, and one of the most concentrated natural forms of GLA. Borage oil is not stable and its active components undergo degradation. The microcapsules of the invention contain about 25% odorless encapsulated Borage oil with increased stability and shelf-life, maintain the GLA in its non-degraded active form, prevent development of distinct malodor during storage of the product, prevent skin irritation, and afford controlled release of high percentage of Borage oil directly to the skin. These microcapsules are indicated as an active ingredient for incorporation in moisturizing creams (especially for dry skin), anti-aging creams, repair formulations, hand creams, and lip-gloss and lip-protecting products.

In some embodiments, the natural extract is Evening Primrose oil (EPO), rich in essential fatty acids such as linoleic acid, gamma-linolenic acid (GLA), oleic acid and others, in their triglyceride form. EPO is not stable and its active components undergo degradation. The microcapsules of the invention contain about 25% odorless encapsulated EPO with increased stability and shelf-life, maintain the GLA in its non-degraded active form, prevent development of distinct malodor during storage of the product, prevent skin irritation, and afford controlled release of high percentage of EPO directly to the skin. These microcapsules are indicated as an active ingredient for incorporation in moisturizing creams (especially for dry skin), anti-wrinkle formulation, repair formulations, hand creams, whitening products, lip-gloss and lip-protecting products.

In some embodiments, the natural extract is Sea Buckthorn (*Hippophae rhamnoides*) oil. This oil contains a unique mix of functional ingredients including a high concentration of carotenoids, palmitoleic acid, sito-sterols and derivatives of vitamins A and E, and is not stable. The microcapsules of the invention contain about 25% encapsulated natural *Hippophae* oil with increased stability and are indicated for incorporation as an active ingredient in anti-aging products, skin treatment formulations, e.g. after peeling, shaving, burns, etc., sunscreen products, eye-zone formulations, and after-sun products.

In some embodiments, the active substance encapsulated is an individual compound isolated from a natural source such as, but not limited to, a coumarin, a chalcone or a flavonoid selected from the group consisting of flavans, flavanols, flavonols, flavones, flavanones, isoflavones, anthocyanidins, and proanthocyanidins.

It should be understood that an active ingredient used in the present embodiments may belong to more than one category as defined herein. Thus, Rutin, defined above as Vitamin P, is a flavonoid, as well Glabridin of the Licorice root extract and the proanthocyanidins of the Grape Seed extract.

In some embodiments, the active substance encapsulated is an essential oil. Essential oils are a class of volatile oils extracted from plants, fruits or flowers by steam, distillation or solvent extraction. Examples of essential oils that can be encapsulated according to the invention include Basil Essential Oil, *Eucalyptus* Essential Oil, Geranium Essential Oil, Grapefruit Essential Oil, Lemon Essential Oil, Peppermint Essential Oil, Tea Tree oil, or mixtures thereof.

In some embodiments, the essential oil is Tea Tree oil, an essential oil with a fresh camphoraceous odor, extracted from the leaves of the tree *Melaleuca alternifolia*. The oil has anti-inflammatory, antibacterial, antifungal, antiviral and antiparasitic properties. Tea Tree oil is beneficial in softening, regenerating and purifying the skin and scalp, in healing burns, disinfecting wounds and for treating spots and insect stings and bites. It is effective against fungal infections such as candidiasis, vaginal infections, fungal nail infections and for hemorrhoids. As a bath additive it may control bacteria in spas and pools. It is also known to reduce hypertrophic scarring and dandruff hair. Tea Tree Oil components include 1-terpinen-ol, responsible for most of the antimicrobial actions, 1,8-cineole, gamma terpinene, p-cymene and other terpenes. Tea Tree Oil is not stable and oxidizes and loses its original activity when incorporated in cosmetic formulations in its naked form, may cause skin irritation and has a very strong original odor due to its volatility. The microcapsules of the present embodiments may contain about 5% odorless encapsulated Tea Tree Oil with increased stability and shelf-life, preventing oxidation of unstable compounds and development of Tea Tree Oil's strong malodor in the formulation, and afford controlled release of high percentage of Tea Tree Oil directly to the skin/scalp. These microcapsules may be indicated as an active ingredient for incorporation in facial care formulations for sensitive and delicate skin, personal hygiene products and shampoos for damaged and delicate hair, and anti-dandruff shampoos.

In some embodiments, the active ingredient encapsulated is an odor (usually a pleasant odor) agent such as fragrances, perfumes, essential oils and compounds extracted therefrom, and volatile natural and synthetic compounds. These agents can be used to impart a pleasant odor to the cosmetic formulation and/or to mask an undesired odor of other components of the formulation.

Agents with odor properties are widely used in topical products. Typically, these agents such as fragrances, perfumes and other volatile materials suffer from instability under specific conditions such as pH of the formulation or their cross-react with other ingredients of the formulation. For these reasons, it is necessary to encapsulate this type of ingredients.

In some embodiments, the volatile compound is Menthol, a monocyclic terpene alcohol obtained from peppermint oil or other mint oils, or prepared synthetically by hydrogenation of thymol. Menthol is a white crystal with a characteristic refreshing mint odor, which provides cosmetic formulations with a fresh sensation, cooling effect, calming qualities and short-term relief. However, Menthol, as a volatile ingredient, has a tendency to evaporate and to change the original content/odor of the formulation. In addition, it is difficult to disperse. Menthol homogeneously in cosmetic formulations and usually requires predispersion with ethanol. The precipitation of Menthol from the formulations, its original strong characteristic odor and its potential cross-linking with other ingredients, are reasons that difficult its use in topical/dental products. The odorless Menthol microcapsules may contain about 10% Menthol. The microcapsules protect the Menthol from oxidation and maintain its original activity after incorporation into cosmetic formulations. They mask Menthol's characteristic odor while maintaining the original smell, preventing it from reacting with other ingredients in the formulation and providing a long lasting sensation/cooling effect upon application on skin. These microcapsules can be homogeneously dispersed in cosmetic formulations without requiring the use of alcohol and are, therefore, indicated as an ingredient for oral hygiene care, e.g. toothpastes, mouth rinses, sun-screen products, cooling after-sun lotions, calming creams and refreshing pre- and after-shave products.

In some of any of the embodiments described herein, the active ingredient encapsulated is a colorant.

The terms "colorant", "color agent" and "pigment" are used herein interchangeably and refer to organic pigments such as synthetic or natural dyes selected from any of the well known FD&C or D&C dyes, inorganic pigments such as metal oxides, or lakes and any combination (blend) thereof. In some exemplary embodiments, the color agent is an inorganic pigment, such as, for example, a metal oxide.

The colorant may be oil-soluble or oil-dispersible or with limited solubility in water. Typically suitable colorants for microencapsulation according to some of any of the embodiments of the present invention include, but are not limited to, organic and inorganic pigments, lakes, natural and synthetic dyes and any combination thereof.

In some embodiments, the color agents are inorganic pigments such as, but not limited to, metal oxides such as iron oxides, titanium dioxide ($TiO_2$), titanium lower oxides, aluminum oxide, zirconium oxides, cobalt oxides, cerium oxides, nickel oxides, chromium oxide (chromium green), zinc oxide and composite metal oxides; metal hydroxides such as calcium hydroxide, iron hydroxides, aluminum hydroxide, chromium hydroxide, magnesium hydroxide and composite metal hydroxides; other colorants such as ferric ammonium ferrocyanide, Prussian blue, iron sulfides, manganese violet, carbon black, mica, kaolin, and any combination thereof.

In some of any of these embodiments, the inorganic pigments are selected from iron oxides, titanium dioxide, zinc oxide, chromium oxide/hydroxide, and mixtures thereof. In a more preferred embodiment, the color agent is iron oxide of any one of the three primary colors—red, yellow or black, or most preferably, a mixture thereof. Optionally, the colorant may comprise, besides the mixture of iron oxides, titanium dioxide, for the purpose of providing any desired final color or shade of color to the composition. Preferably, when encapsulated within the inner core microcapsules, titanium dioxide is used in any one of its mineral forms such as, but not limited to, anatase, brookite or rutile, or any combination thereof.

In some other embodiment, the colorants are Lake organic pigments produced by precipitation of a natural or synthetic dye with a metallic salt such as aluminum, calcium or barium salts. Such colorants are typically oil-dispersible and widely used in cosmetics. Examples of Lake pigments include, but are not limited to, Indigo Lakes, Carmine Lakes, lakes from the series of the well-known FD&C and D&C dyes such as D&C Red 21 Aluminum Lake, D&C Red 7 Calcium Lake.

Exemplary additional active agents according to this embodiment of present invention include, without limitation, one or more, or any combination of an antibiotic agent, an antimicrobial agent, an anti-acne agent, an anti-aging agent, a wrinkle-reducing agent, a skin whitening agent, a sebum reducing agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, an antineoplastic agent, an immunomodulator, an interferon, an antidepressant, an anti histamine, a hormone and an anti-dandruff agent.

Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14, 304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilorate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs), corticotropin-releasing factor (CRF) antagonists, α-adreno-receptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amil-triptylinoxide, amoxapine, desipramine, maprotiline, nor-triptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff agents include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of dermatological active ingredients usable in context of the present invention include jojoba oil and aromatic oils such as methyl salicylate, wintergreen, peppermint oil, bay oil, *Eucalyptus* oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

It is to be notes that any other active agent, including agents described herein as additives, can be encapsulated in the microcapsules as described herein.

As described herein, the active agent is included in a core of the inner core microcapsules. In some embodiments, the inner core microcapsules, including the active agent, the wall forming agent and any additional agents are as described in U.S. Pat. No. 6,932,984, including any embodiments and combination thereof described therein.

The amount of the inner core microcapsules is usually within a range of from about 10% to about 80%, or from about 10% to about 70%, or from about 10% to about 60%, or from about 10% to about 50%, or from about 10% to about 40%, by weight, including any subranges and any intermediate values therebetween. A person skilled in the art would recognize the amount of the active agent, by weight percents, of the total weight of the microcapsules.

In some of any of the embodiments described herein, the microcapsule contains one active agent or a mixture of two or more active agents, either encapsulated individually and/or one or more active agents may be encapsulated together within the core of double- or multi-layer microcapsules.

Active Agent-Containing Composition:

According to an aspect of some embodiments of the present invention there is provided a composition which comprises a plurality of microcapsules, at least a portion of the microcapsules are multi-layer microcapsules which comprise an inner core microcapsule comprising at least one active agent and a first shell comprised of a first wall-forming polymeric material enveloping the core, and one or more outer shells enveloping the inner ore microcapsule, as described in any one of the embodiments described herein. Such a composition is also referred to herein as an active agent-containing composition or simply as a composition.

In some embodiments, at least 10%, at least 20%, at least 30%, at least 40%, at least 50%, at least 60%, at least 70%, at least 80%, at least 90%, at least 95%, at least 98%, or at least 99%, or all of the plurality of microcapsules in the composition are active agent-containing microcapsules as described in any one of the embodiments described herein.

"Composition" as used herein refers to a plurality of microcapsules, which can be the same or different, which, when different, can feature a plurality or variety of features. In accordance with embodiments of the present invention, at least a portion of the plurality of microcapsules exhibits all the technical features characterizing a microcapsule as described herein, in any one of the embodiments thereof, for example, having at least two outer shells, encapsulating an active agent as described herein, comprising a fatty acid salt, comprising a dispersing agent, being breakable upon rubbing on the skin and being opaque.

The term "at least a portion" means at least 20%, at least 50%, at least 70%, at least 60%, at least 80%, at least 90%, at least 95%, at least 98%, at least 99% or all of the microcapsules being the multi-layer, active agent-containing microcapsules, as described in any one of the respective embodiments herein.

In some embodiments, the active agent-containing microcapsules as described herein in the composition can be the same, or can differ from one another by the active agent encapsulated therein and/or by the number and/or type of wall-forming polymeric material comprising the shells.

In at least part or portion of the plurality of microcapsules of the composition provided herein, the active agent may be the same or different, and/or the microcapsules may encapsulate a mixture of active agents in their core.

In some embodiments related to the composition of the invention, particularly to that portion of plurality of microcapsules in the composition that exhibits the combination of technical features that characterize a multi-layer microcapsule of the invention, each microcapsule can contain one or a mixture of two of more active agents. In some other embodiments, microcapsules containing one active agent can be mixed with microcapsules containing another active or a mixture of active agents, within the composition.

Each of the microcapsules described herein can be used in any combination, and with each of the embodiments described herein for the formulation/composition containing same.

Exemplary Microcapsules and Compositions:

In some exemplary embodiments of the present invention, a second wall-forming material comprises magnesium stearate in an amount within a range of from 1.0% to 2.0%, $TiO_2$ in an amount within a range of 30 5 to 75% and a dispersing agent (e.g., isopropyle myristate of propylene glycol stearate) in an amount within a range of from 4% to 6%, by weight, of the total weight of the microcapsule.

In some exemplary embodiments, a multi-layer microcapsule as described herein encapsulates comprises a wall-forming material comprising an acrylate/ammonium methacrylate copolymer, either alone or in combination with cellulose ester such as cellulose actate.

In some exemplary embodiments, a multi-layer microcapsule as described herein comprises inner microcapsules comprising an active agent in an amount of about 30-50% by weight, a wall-forming polymer or copolymer in an amount of 10-30% by weight, magnesium stearate in an amount of 0.5-1%, $TiO_2$ in an amount of 25-50% and isopropyl myristate in an amount of 1-6%, by weight.

In some exemplary embodiments, at least a portion of a plurality of microcapsules comprised in the composition of the invention are double-layer microcapsules which comprise $TiO_2$ as the opaque substance in an amount of about 30-45% by weight, and the wall-forming material comprises acrylate/ammonium methacrylate copolymer (e.g., Udragit® RSPO) in a total amount of about 10-30% by weight, magnesium stearate in the amount of 1%, and inner microcapsules comprising an active agent in an amount of 36-45% by weight of total capsule's weight.

In some exemplary embodiments, at least a portion of a plurality of microcapsules comprised in the composition of the invention are compositions comprising double layer microcapsules comprising the dispersing agent isopropyl myristate in an amount of 3.0% by weight.

In some exemplary embodiments, a multi-layer microcapsule as described herein comprises inner microcapsules comprising an active agent in an amount of about 10-30% by weight, a wall-forming polymer or copolymer in an amount of 5-15% by weight, magnesium stearate in an amount of 1-2% by weight, $TiO_2$ in an amount of 30-75% by weight, and propylene glycol stearate in an amount of 4-6%, by weight, of the total weight of the composition.

In some exemplary embodiments, at least a portion of a plurality of microcapsules comprised in the composition of the invention are double-layer microcapsules which comprise $TiO_2$ as the opaque substance in an amount of about 30-75% by weight, and the wall-forming material comprises acrylate/ammonium methacrylate copolymer (e.g., Udragit® RSPO) in combination with ethyl cellulose a total amount of about 5-15% by weight, magnesium stearate in the amount of 2%, and inner microcapsules in an amount of 10-30% by weight of total capsule's weight.

In some exemplary embodiments, at least a portion of a plurality of microcapsules comprised in the composition of the invention are double-layer microcapsules which comprise $TiO_2$ as the opaque substance in an amount of about 70-75% by weight, and the wall-forming material comprises ethyl cellulose a total amount of about 5-10% by weight, magnesium stearate in the amount of 2%, and inner microcapsules in an amount of 10-15% by weight of total capsule's weight.

In some exemplary embodiments, at least a portion of a plurality of microcapsules comprised in the composition of the invention are active agent-containing compositions comprising double layer microcapsules in which the second wall-forming material comprises, or consist of, cellulose acetate, and comprising the dispersing agent propylene glycol stearate in an amount of 4-6% by weight of the total weight of the microcapsule.

The Process:

The process used for the preparation of the microcapsules of the invention as described herein is a modification of the microencapsulation solvent removal method disclosed, for example, in U.S. Pat. Nos. 6,932,984 and 7,838,037 and WO 2012/156965, which are incorporated by reference as if fully set forth herein. According to this technology, the active ingredient is found in the core of the microcapsule. This technique seals each micro-capped ingredient from chemical and cross-link reactions, degradation, color change or loss of potency during production, and for extended periods in storage. The solvent removal process is based on four main steps as follows:
(i) preparing a homogeneous organic solution comprising the encapsulated agent, a wall-forming polymeric material, an opaque substance, a plasticizer and an organic solvent that is partially miscible in water;
(ii) preparing an emulsion of an aqueous continuous phase containing an emulsifier and saturated with the same organic solvent of the organic solution;
(iii) mixing the homogeneous organic solution with the aqueous emulsion, under high shear stirring to thereby form a multi-component emulsion; and
(iv) extracting the organic solvent by adding to the emulsion formed in step (iii) an amount of water which initiates extraction of the organic solvent from the emulsion, thereby obtaining the microcapsules.

As taught in U.S. Pat. No. 7,838,037, double-layer and triple-layer microcapsules are formed by first modifying the surface of the single layer microcapsules formed according to steps (i)-(iv) and then subjecting the surface-modified inner core microcapsules to one or more cycles of steps (i)-(iv), when the inner core microcapsules are dispersed in the organic solution together with the wall-forming material.

However, in some embodiments of the modified method provided herein, the inner core microcapsules as well as the opaque substance such as $TiO_2$ are dissolved or dispersed in the continuous aqueous emulsion. In addition, a fatty acid salt such as magnesium stearate is added to the organic solution. By shifting $TiO_2$ to the aqueous phase, and adding magnesium stearate to the organic solution, double- and triple-layer microcapsules were obtained wherein the $TiO_2$ uniformly coated the outer polymeric shell thereby providing a masking layer to the inner core microcapsules. Thus, in some embodiments, the multi-layer microcapsules according to the present invention can be prepared by the modified solvent removal method comprising the following steps:
(a) contacting a first organic phase comprising a second wall-forming polymer or copolymer, a fatty acid salt, optionally a dispersing agent and a plasticizer, and a first partially water-miscible organic solvent, with a first aqueous solution saturated with said organic solvent and comprising an emulsifier, an opaque substance and single-layer microcapsules containing one or more active agents and a first wall-forming agent, to thereby obtain a first multi-component emulsion;
(b) adding to the formed emulsion an amount of water which initiates extraction of the organic solvent from the emulsion, thereby obtaining double-layered microcapsules; and
(c) optionally repeating steps (a) and (b), using a second, third, and so on, organic phases and aqueous continuous phases, thereby obtaining multi-layered microcapsules.

In further steps, the microcapsules are isolated following step (b), dried and sifted to thereby obtain a free flowing powder of the microcapsules.

These steps are further detailed as follows:

The homogenous solution prepared in step (a) is obtained by preparing an organic solution or dispersion of a wall-forming polymeric material as described in any one of the respective embodiments described herein, in an organic solvent that is partially miscible in water and is capable of dissolving or dispersing the wall-forming polymer. In exemplary embodiments, the organic solvent is an organic solvent approved for topical applications, such as, but not limited to, ethyl acetate, ethanol, ethyl formate, or any combination thereof. In some embodiments, the organic solvent is ethyl acetate.

The fatty acid salt is as described in any one of the respective embodiments described herein. An optional dispersion agent is as described in any one of the respective embodiments described herein.

When a plasticizer is used, it is usually selected from tricaprylin, trilaurin, tripalmitin, triacetin, triethyl citrate, acetyltriethyl citrate, paraffin oil, or any combination thereof.

The components of the organic solution are mixed/stirred until a homogeneous, optionally transparent, solution is obtained.

The first aqueous continuous phase is saturated with the organic solvent that forms the organic solution, and typically comprises an emulsifier, the opaque substance and single-layer microcapsules containing one or more active agents and a first wall-forming material (inner core microcapsules, as described herein).

The opaque substance is as described in any one of the respective embodiments described herein. In preferred embodiments, the opaque substance is $TiO_2$.

The inner e.g. single-layer core microcapsules, may be obtained by the known solvent removal method, as described, for example, in U.S. Pat. No. 6,932,984.

The organic solution and the first aqueous continuous phase are mixed under low sheer stirring to thereby form a multi component emulsion.

In step (b), an amount of water is added to the multi component emulsion prepared in (a), thereby extracting the organic solvent and allowing the double-layer microcapsules to form.

If triple or other multi-layer microcapsules are desired, steps (a) and (b), are repeated using a second, third, and so on, organic phases and aqueous continuous phases, wherein the organic solvent may be the same or different, the wall-forming material, the plasticizer as well as the opaque substance, the fatty acid salt and the dispersing agent may be the same or different.

In the context of embodiments of the invention, the term "low sheer stirring" refers to a mixing at about 100-800 rpm, preferably at about 300-600 rpm.

In some exemplary embodiments, the ingredients employed in the process comprise the wall-forming polymer acrylate/ammonium methacrylate copolymer, ethyl acetate as the organic solvent partially miscible with water, the dispersing agent isopropyl myristate, the fatty acid salt magnesium stearate and the opaque substance titanium dioxide.

In some other embodiments of the modified method provided herein, the inner core microcapsules as well as the opaque substance such as $TiO_2$ are dissolved or dispersed in the organic phase, and a fatty acid salt such as magnesium stearate also is added to the organic solution. These embodiments preferably relate to microcapsules which comprise cellulose acetate in one or more of the outer shells (e.g., the second and/or most outer shell). The present inventors have demonstrated that by using cellulose acetate as one of the wall-forming polymeric materials, an improved opacity is obtained also when the opaque substance such as $TiO_2$ is included in the organic phase, such that in the obtained double- and triple-layer microcapsules the $TiO_2$ uniformly coats the outer polymeric shell thereby providing a masking layer to the inner core microcapsules. Thus, in some embodiments, the multi-layer microcapsules according to the present invention can be prepared by the modified solvent removal method comprising the following steps:

(a) contacting a first organic phase comprising a second wall-forming polymer or copolymer, a fatty acid salt, an opaque substance and single-layer microcapsules containing one or more active agents, and optionally a dispersing agent and a plasticizer, and a first partially water-miscible organic solvent, with a first aqueous solution saturated with said organic solvent and typically comprising an emulsifier, to thereby obtain a first multi-component emulsion;

(b) adding to the formed emulsion an amount of water which initiates extraction of the organic solvent from the emulsion, thereby obtaining double-layered microcapsules; and (c) optionally repeating steps (a) and (b), using a second, third, and so on, organic phases and aqueous continuous phases, thereby obtaining multi-layered microcapsules.

In further steps, the microcapsules are isolated following step (b), dried and sifted to thereby obtain a free flowing powder of the microcapsules.

These steps are further detailed as follows:

The homogenous solution prepared in step (a) is obtained by preparing an organic solution or dispersion of a second wall-forming polymeric material as described in any one of the respective embodiments described herein, in an organic solvent that is partially miscible in water and is capable of dissolving or dispersing the second wall-forming polymer. In exemplary embodiments, the organic solvent is an organic solvent approved for topical applications, such as, but not limited to, ethyl acetate, ethanol, ethyl formate, or any combination thereof. In some embodiments, the organic solvent is ethyl acetate.

The fatty acid salt is as described in any one of the respective embodiments described herein. An optional dispersion agent is as described in any one of the respective embodiments described herein.

The opaque substance is as described in any one of the respective embodiments described herein. In preferred embodiments, the opaque substance is $TiO_2$, optionally in combination with boron nitride.

The inner e.g. single-layer core microcapsules, may be obtained by the known solvent removal method, as described, for example, in U.S. Pat. No. 6,932,984.

When a plasticizer is used, it is usually selected from tricaprylin, trilaurin, tripalmitin, triacetin, triethyl citrate, acetyltriethyl citrate, paraffin oil, or any combination thereof.

The components of the organic solution are mixed/stirred until a homogeneous, optionally transparent, solution is obtained.

The first aqueous continuous phase is saturated with the organic solvent that forms the organic solution, and typically comprises an emulsifier. The organic solution and the first aqueous continuous phase are mixed under low sheer stirring to thereby form a multi component emulsion.

Further steps of these embodiments are as described hereinabove.

Topical Formulations:

In some embodiments, the composition provided herein is used in cosmetic, cosmeceutical or pharmaceutical formulations such as skin care formulations, make-up or dermatological or other topical pharmaceutical formulations, comprising the microcapsules as described herein (e.g., a composition as described herein). The formulation can optionally and preferably further comprise a carrier, and optionally additional active agents and/or additives.

As used herein a "formulation" refers to a vehicle in the form of emulsion, lotion, cream, gel, powder, etc., that comprises the active agent-containing microcapsules as described herein with physiologically acceptable carriers and excipients and optionally other chemical components such as cosmetic, cosmeceutic or pharmaceutical agents (e.g., drugs).

As used herein, the term "physiologically acceptable" means approved by a regulatory agency of the Federal or a state government or listed in the U.S. Pharmacopeia or other generally recognized pharmacopeia for use in animals, and more particularly in humans.

Herein, the phrase "physiologically suitable carrier" refers to an approved carrier or a diluent that does not cause significant irritation to an organism and does not abrogate the biological activity and properties of a possible active agent.

Herein the term "excipient" refers to an inert substance added to a pharmaceutical composition to further facilitate processes and administration of the active ingredients.

In some embodiment of the present invention, the cosmetic or cosmeceutical formulation is formulated in a form suitable for topical application on the applied area.

By selecting the appropriate carrier and optionally other ingredients that can be included in the composition, as is detailed hereinbelow, the compositions of the present embodiments may be formulated into any form typically employed for topical application.

The formulations can be water-based, oil-based or silicon-based.

The formulations as described herein can be, for example, skin care products, make-up products (including eye shadows, make-up, lipstick, lacquer, etc., or any other product as described herein).

In some embodiments, a formulation as described is in a form of a cream, an ointment, a paste, a gel, a lotion, a milk, an oil, a suspension, a solution, an aerosol, a spray, a foam, a powder (e.g., a pressed powder or a loose powder) or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

The preparation of the formulation can be carried out by mixing and homogenizing all the ingredients except for the active agent-containing microcapsules, and adding the active agent-containing microcapsules at the end, followed by low shear mixing of the mixture.

The multi-layer microcapsules of the invention can be used in pharmaceutical compositions for topical application, which include, for example, pharmaceutically active agents for dermatological or transdermal applications.

In any of the formulations described herein, additional agents and/or additives can be included. These agents and/or additives and can be encapsulated or non-encapsulated.

In some embodiments, one or more of these agents and/or additives is encapsulated.

In some of these embodiments, the agents and/or additives are encapsulated using microcapsules as described in any one of U.S. Pat. Nos. 6,932,984 and 7,838,037, and WO 2009/138978.

Some non-limiting representative examples of additives and/or agents include humectants, deodorants, antiperspirants, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

Representative examples of humectants include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propyleneglycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

Suitable pH adjusting agents include, for example, one or more of adipic acids, glycines, citric acids, calcium hydroxides, magnesium aluminometasilicates, buffers or any combinations thereof.

Representative examples of deodorant agents include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sunless tanning agents include, without limitation, dihydroxyacetone, glyceraldehyde, indoles and their derivatives. The sunless tanning agents can be used in combination with the sunscreen agents.

The chelating agents are optionally added to formulations so as to enhance the preservative or preservative system. Preferred chelating agents are mild agents, such as, for example, ethylenediaminetetraacetic acid (EDTA), EDTA derivatives, or any combination thereof.

Suitable preservatives include, without limitation, one or more alkanols, disodium EDTA (ethylenediamine tetraacetate), EDTA salts, EDTA fatty acid conjugates, isothiazolinone, parabens such as methylparaben and propylparaben, propyleneglycols, sorbates, urea derivatives such as diazolindinyl urea, or any combinations thereof.

Suitable emulsifiers include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propyleneglycol (PG), propyleneglycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants include, for example, steroidal and non steroidal anti-inflammatory agents or other materials such as aloe vera, chamomile, alpha-bisabolol, cola nitida extract, green tea extract, tea tree oil, licorice extract, allantoin, caffeine or other xanthines, glycyrrhizic acid and its derivatives.

It is expected that during the life of a patent maturing from this application many relevant active agents, wall-forming materials and opaque substances will be developed and the scope of the term "active agent", "wall-forming polymer" and "opaque substance" is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The terms "weight percents" or "% by weight" or "% wt." are used herein interchangeably.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

The novel encapsulation methodology presented herein has been demonstrated for encapsulation of color agents, as described in the following examples. It is noted that this methodology can be applied to any of the active agents described herein.

Example 1

Preparation of Double-Layer Microcapsules Containing Red Colorant Preparation of Organic Phase/Master Batch (MB)

An organic phase (herein referred to interchangeably as "master batch" (MB)) was prepared by gradually adding 10 grams of the wall-forming polymer acrylate/ammonium methacrylate copolymer (EUDRAGIT® RSPO) into 117.4 grams of ethyl acetate at room temperature, and stirring the obtained mixture until the a homogeneous and transparent mixture was obtained (about 10 minutes). One gram of magnesium stearate was then added to the solution, under stirring, for 2 minutes and, finally, 3 grams of boron nitride was added for additional 2-minute stirring. The components of the MB are presented in Table 1.

TABLE 1

Master batch constituents

| | Material | Loading for 100 grams MB |
|---|---|---|
| 1 | Acrylate/ammonium methacrylate copolymer (Udragit RSPO, Evonik Industries, Germany) | 10.0 |
| 2 | Boron nitride (Dandong Chemical Engineering Institute Co., Ltd, China) | 3.0 |

TABLE 1-continued

Master batch constituents

| | Material | Loading for 100 grams MB |
|---|---|---|
| 3 | Magnesium stearate (Faci Asia Pacific Pte Ltd, Singapore) | 1.0 |
| 4 | Ethyl acetate (Gadot, Israel) | 117.4 |

Preparation of the Emulsion:

An aqueous solution was prepared by mixing water (550 grams) with polyvinyl alcohol 4% solution (PVA 4%; 36.7 grams) such that the final concentration of PVA in the water phase was 0.25% by weight. Then, the opaque substance titanium dioxide ($TiO_2$; 41 grams) was added under stirring (450 rpm), first for 5-minute stirring and then for additional 8-minute homogenization (2500 rpm). Ethyl acetate (65.2 grams) was added to the water phase while stirring for 2 minutes at 450 rpm. Then, single-layer microcapsules containing a red colorant (diiron dioxide; 45 grams), herein termed "Red Timers", prepared as described in U.S. Pat. No. 6,932,984 (with or without a plasticizer), were added gradually to the water phase for 2-minute stirring. These microcapsules were covered or enveloped by a further layer of wall-forming material, by gradually adding the MB described above (131.4 grams), containing the dissolved or dispersed polymer, into the ethyl acetate/water emulsion under stirring of 450 rpm, and further stirring for additional 2 minutes. The ratio MB:emulsion (w/w) was 1:3. The components of the emulsion are presented in Table 2.

TABLE 2

Emulsion constituents

| | Material | Loading (grams) |
|---|---|---|
| 1 | Water | 550.0 |
| 2 | PVA (Mowiol 4-88, KSE solution 4%; Kuraray America, Inc., USA) | 36.7 |
| 3 | Ethyl Acetate | 65.2 |
| 4 | $TiO_2$ (RC402, Sachtleben, Germany) | 41.0 |
| 5 | Red diiron trioxide | 45.0 |
| 6 | MB | 131.4 |

Extraction of the Organic Solvent:

The extraction medium was composed of 3,796 grams water, into which the emulsion described above (869.6 grams) above was gradually added in a 10 L pail under stirring at 150 rpm, using a manual pump. The extraction phase was further stirred for additional 15 minutes. The resulting mixture was left to sediment for about 5 hours at room temperature. The components of the extraction medium are presented in Table 3.

TABLE 3

Extraction medium constituents

| | Material | Loading (grams) |
|---|---|---|
| 1 | Emulsion Extraction fluid | 869.6 |
| 2 | Water | 3,796.0 |

Washing, Drying and Sifting of the Microcapsules:

The obtained microcapsules of step 1.3 above were separated by vacuum filtration. The upper phase liquid was decanted from the pail, the remaining suspension was shaken and then filtered, and the sediment was rinsed on a filter with 400 ml water. The suspension was transferred to a drying vessel and the microcapsules were stored at 4° C. In the drying stage, the microcapsules were freeze dried (lyophilized) for 48 hours.

In the sifting stage, the dried microcapsules were sifted using automatic sifter "Ari j-Levy", Sifter MIC. 300. The sifted microcapsules were stored in an appropriate container in a refrigerator.

Example 2

Preparation of Double-Layer, Plasticizer-Containing Microcapsules Containing Red Colorant Double-layered microcapsules comprising inner core microcapsules containing a red colorant and an outer shell comprising a plasticizer (triethyl citrate) were prepared as described in Example 1 above, except for the use of the plasticizer.

Thus, the master batch (MB) was prepared by gradually adding the wall-forming polymer acrylate/ammonium methacrylate copolymer (EUDRAGIT® RSPO; 14.5 grams) into 117.4 grams of ethyl acetate at room temperature, while stirring well until the mixture was homogeneous and transparent (about 10 minutes). A plasticizer, triethyl citrate (4.5 grams), was thereafter added to the mixture under stirring. One gram of magnesium stearate was then added to the solution under stirring for 2 minutes and, finally, 3 grams of boron nitride was added for additional 2-minute stirring.

As described in Example 1, the emulsion was prepared by mixing water (550 grams) with polyvinyl alcohol 4% solution (PVA 4%; 36.7 grams) to a final concentration 0.25% PVA, followed by addition of $TiO_2$ (41 grams) under stirring (450 rpm), first for 5-minute stirring and then for additional 8-minute homogenization (2500 rpm). Then followed the addition of ethyl acetate (65.2 grams; stirring for 2 minutes at 450 rpm) and the gradual addition of Red Inners (single-layer microcapsules containing a the red colorant diiron trioxide; 36 grams). These microcapsules were covered or enveloped by a further layer of wall-forming material containing a plasticizer, by gradually adding the MB of the former step under stirring of 450 rpm, and further stirring for additional 2 minutes. The ratio MB:emulsion (w/w) was 1:3.

The extraction of ethyl acetate and formation of double-layered microcapsules, followed by washing, drying and sifting of the microcapsules were carried out as described in Example 1. The main components of the obtained microcapsules are presented in Table 4.

TABLE 4

| | Material | Loading for 100 grams MB |
|---|---|---|
| 1 | Acrylate/ammonium methacrylate copolymer (Udragit RSPO, Evonik Industries, Germany) | 14.5 |
| 2 | Triethyl citrate | 4.5 |
| 3 | Boron nitride (Dandong Chemical Engineering Institute Co., Ltd, China) | 3.0 |
| 4 | Magnesium stearate (Faci Asia Pacific Pte Ltd, Singapore) | 1.0 |
| 5 | $TiO_2$ (RC402, Sachtleben, Germany) | 41 |
| 6 | Red diiron trioxide | 36 |

Example 3

Preparation of Double-Layer, Plasticizer-Containing Microcapsules Containing Yellow Colorant Double-layered microcapsules comprising inner core microcapsules containing a yellow colorant (iron oxide) and an outer shell comprising a plasticizer (triethyl citrate) were prepared as described in Examples 1 and 2 above, using yellow iron oxide capsules (yellow inners), prepared as described in U.S. Pat. No. 6,932,984 (with or without a plasticizer), instead of the red inners. The main components of the obtained microcapsules are presented in Table 5.

TABLE 5

| | Material | Loading for 100 grams MB |
|---|---|---|
| 1 | Acrylate/ammonium methacrylate copolymer (Udragit RSPO, Evonik Industries, Germany) | 20.5 |
| 2 | Triethyl citrate | 4.5 |
| 3 | Boron nitride (Dandong Chemical Engineering Institute Co., Ltd, China) | 3.0 |
| 4 | Magnesium stearate (Faci Asia Pacific Pte Ltd, Singapore) | 1.0 |
| 5 | $TiO_2$ (RC402, Sachtleben, Germany) | 35 |
| 6 | Yellow iron oxide | 36 |

Example 4

Preparation of Double-Layer, Plasticizer-Containing Microcapsules Containing Black Colorant Double-layered microcapsules comprising inner core microcapsules containing a black colorant (triiron tetraoxide) and an outer shell comprising a plasticizer (triethyl citrate) were prepared as described in Examples 1 and 2 above, while using black inners, prepared as described in U.S. Pat. No. 6,932,984 (with or without a plasticizer), instead of the red inners. The main components of the obtained microcapsules are presented in Table 6.

TABLE 6

| | Material | Loading for 100 grams MB |
|---|---|---|
| 1 | Acrylate/ammonium methacrylate copolymer (Udragit RSPO, Evonik Industries, Germany) | 14.5 |
| 2 | Triethyl citrate | 4.5 |
| 3 | Boron nitride (Dandong Chemical Engineering Institute Co., Ltd, China) | 3.0 |
| 4 | Magnesium stearate (Faci Asia Pacific Pte Ltd, Singapore) | 1.0 |
| 5 | $TiO_2$ (RC402, Sachtleben, Germany) | 41 |
| 6 | Black iron oxide | 36 |

Example 5

Preparation of Double-Layer Microcapsules Comprising Isopropyl Myristate and Red Colorant The present inventors have uncovered that by including isopropyl myristate (IPM) in the wall-forming material of double-layered microcapsules, softer, and more readily spreadable, microcapsules are obtained. Upon application to the skin, the microcapsules that contained IPM broke and released their content more readily. In exemplary microcapsules, IPM was used in an amount of about 5 weight percents of total weight of the microcapsule. When the microcapsules break, the encapsulated colorant is released and coated with the oily IPM which thereby accounts for smoother and a uniform spread of the colorant on the skin. Isopropyl myristate is thus considered as acting both as a plasticizer and a dispersing agent.

According to the exemplary encapsulation process provided herein, IPM is added to the master batch (MB), at the expense of the $TiO_2$ added to the emulsion.

Thus, for the preparation of colorant- and IPM-containing microcapsules, the master batch was prepared by gradually adding the wall-forming polymer acrylate/ammonium methacrylate copolymer (UDRAGIT® RSPO; 14.5 grams) into ethyl acetate at room temperature, while stirring well until the mixture was homogeneous and transparent (about 10 minutes). A plasticizer, triethyl citrate (4.5 grams) was added under stirring. Then, IPM was added and the organic phase was stirred for 2 minutes. One gram of magnesium stearate was then added to the solution under stirring for 2 minutes and, finally, 3 grams of boron nitride were added for additional 2-minute stirring.

The emulsion formation, mixing thereof with the MB and the following extraction of the organic solvent, were carried out as described in Examples 1 and 2. Washing, drying and sifting of the microcapsules were carried out as described in Example 1. The main components of the obtained microcapsules are presented in Table 7.

TABLE 7

| | Material | Loading for 100 grams MB |
|---|---|---|
| 1 | Acrylate/ammonium methacrylate copolymer (Udragit RSPO, Evonik Industries, Germany) | 14.5 |
| 2 | Triethyl citrate | 4.5 |
| 3 | Isopropyl Myristate | 5 |
| 4 | Boron nitride (Dandong Chemical Engineering Institute Co., Ltd, China) | 3.0 |
| 5 | Magnesium stearate (Faci Asia Pacific Pte Ltd, Singapore) | 1.0 |
| 6 | $TiO_2$ (RC402, Sachtleben, Germany) | 36 |
| 7 | Red diiron trioxide | 36 |

Example 6

Preparation of Double-Layer Microcapsules Comprising Isopropyl Myristate and Yellow Colorant Double-layered microcapsules comprising inner core microcapsules containing a yellow colorant (iron oxide), as described in Example 3, and IPM, and an outer shell comprising a plasticizer (triethyl citrate) were prepared as described in Example 5 above. The main components of the obtained microcapsules are presented in Table 8.

TABLE 8

| | Material | Loading for 100 grams MB |
|---|---|---|
| 1 | Acrylate/ammonium methacrylate copolymer (Udragit RSPO, Evonik Industries, Germany) | 20.5 |
| 2 | Triethyl citrate | 4.5 |
| 3 | Isopropyl Myristate | 5 |
| 4 | Boron nitride (Dandong Chemical Engineering Institute Co., Ltd, China) | 3.0 |
| 5 | Magnesium stearate (Faci Asia Pacific Pte Ltd, Singapore) | 1.0 |
| 6 | $TiO_2$ (RC402, Sachtleben, Germany) | 30 |
| 7 | Yellow iron oxide | 36 |

Example 7

Preparation of Double-Layer Microcapsules Comprising Isopropyl Myristate and Black Colorant Double-layered microcapsules comprising inner core microcapsules containing a black colorant (triiron tetraoxide), as described in Example 4, and IPM, and an outer shell comprising a plasticizer were prepared as described in Example 5 above. The main components of the obtained microcapsules are presented in Table 9.

TABLE 9

| | Material | Loading for 100 grams MB |
|---|---|---|
| 1 | Acrylate/ammonium methacrylate copolymer (Udragit RSPO, Evonik Industries, Germany) | 14.5 |
| 2 | Triethyl citrate | 4.5 |
| 3 | Isopropyl Myristate | 5 |
| 4 | Boron nitride (Dandong Chemical Engineering Institute Co., Ltd, China) | 3.0 |
| 5 | Magnesium stearate (Faci Asia Pacific Pte Ltd, Singapore) | 1.0 |
| 6 | $TiO_2$ (RC402, Sachtleben, Germany) | 36 |
| 7 | Black triiron tetraoxide | 36 |

Example 8

Preparation of Double-Layer Cellulose Acetate Microcapsules Containing Red Iron Oxide (Cameleon Red Microcapsules Preparation of Organic Phase/Master Batch (MB):

An organic phase (herein referred to interchangeably as "master batch" (MB)) was prepared by gradually adding the wall-forming polymers Cellulose Acetate and then Acrylate/Ammonium Methacrylate Copolymer under stirring into ethyl acetate at room temperature and stirring the mixture until it was homogeneous and transparent. Propylene Glycol Stearate, acting as a dispersant/plasticizer, as described herein for IPM, was then added to the solution under stirring for about 5 minutes, followed by the addition of Magnesium Stearate (MgSt) and stirring for about 5 minutes. Thereafter, titanium dioxide ($TiO_2$) was added to the mixture under stirring for about 5 minutes and the obtained mixture was homogenized for about 8 minutes. Red inner capsules (as described in Example 1) were then added under stirring for about 5 minutes.

The components and the respective amounts of the MB ingredients are presented in Table 10 below.

TABLE 10

| Master batch constituents | |
|---|---|
| Material | Loading for 100 grams MB |
| Cellulose Acetate | 7.5 |
| Acrylate/Ammonium Methacrylate Copolymer | 4 |
| Propylene Glycol Stearate | 4 |
| Magnesium Stearate | 2 |
| Titanium Dioxide | 54.5 |
| Red Inner capsules | 28 |
| Ethyl acetate | 233.3 |

Preparation of the Emulsion:

Emulsion was prepared by adding to water, while stirring, a 4% aqueous solution of Polyvinyl Alcohol (PVA), followed by a 4% aqueous solution of Ceteareth 25 (a polyoxyethylene ether, acting as an emulsifier, and thereafter adding to the aqueous phase ethyl acetate, under stirring for about 1-2 minutes. The MB described above was then gradually added into the emulsion under stirring at about 400 RPM for 2 minutes. The ratio between the Master Batch and the emulsion (w/w) was 1:3. The components and respective amounts of the emulsion are presented in Table 11.

TABLE 11

Emulsion constituents

| Material | Loading (grams) |
|---|---|
| Water | 808 |
| PVA | 90 |
| Ceteareth 25 | 2.25 |
| Ethyl Acetate | 100 |
| MB | 333.3 |

Extraction of the Organic Solvent:

The extraction medium was composed of a mixture of water and 4% aqueous solution of PVA (i.e., a final concentration of PVA in the extraction fluid was 0.2% PVA). The emulsion described above was gradually added into the extraction fluid in a 15 L pail under stirring at 150 RPM using a manual pump, and the obtained mixture was stirred for additional 15 minutes. The resulting mixture was left to sediment for about 24 hours at 25° C. The components and amounts of the extraction medium are presented in Table 12.

TABLE 12

Extraction medium constituents

| Material | Loading (grams) |
|---|---|
| Emulsion | 1333.3 |
| Water | 4180 |
| 4% PVA solution | 144 |

Washing, Drying and Sifting of the Microcapsules:

The obtained microcapsules were separated either by sedimentation or vacuum filtration. In the sedimentation procedure, the upper liquid phase from the pail was decanted and the remaining suspension was shaken and transferred to a drying vessel. In the filtration procedure, the upper phase liquid was decanted from the pail, the remaining suspension was shaken and then filtered, and the sediment was rinsed on the filter with 400 ml water. The suspension was transferred to a drying vessel. In the drying stage, the microcapsules were freeze dried (lyophilized) for up to 48 hours.

In the sifting stage, the dried microcapsules were sifted using automatic sifter "Ari j-Levy", Sifter MIC. 100. The sifted microcapsules were stored in an appropriate container in room temperature.

The main components of the obtained microcapsules are presented in Table 13.

TABLE 13

| | Material | Loading for 100 grams |
|---|---|---|
| 1 | Cellulose Acetate | 7.5 |
| 2 | Acrylate/Ammonium Methacrylate Copolymer | 4.0 |

TABLE 13-continued

| | Material | Loading for 100 grams |
|---|---|---|
| 3 | Propylene Glycol Stearate | 4.0 |
| 4 | Magnesium Stearate | 2. |
| 5 | Titanium Dioxide | 54.5 |
| 6 | Red Inner capsules | 28 |

Example 9

Preparation of Double-Layer Cellulose Acetate Microcapsules Containing Black Iron Oxide (Cameleon Black Microcapsules)

MB was prepared as described in Example 9, using black inner capsules, as described in Example 4. Double layered microcapsules comprising black inner core were then prepared using an emulsion, extraction medium and process as described herein in Example 8. The main components of the obtained microcapsules are presented in Table 14.

TABLE 14

| | Material | Loading for 100 grams |
|---|---|---|
| 1 | Cellulose Acetate | 7.5 |
| 2 | Acrylate/Ammonium Methacrylate Copolymer | 4.0 |
| 3 | Propylene Glycol Stearate | 4.0 |
| 4 | Magnesium Stearate | 2 |
| 5 | Titanium Dioxide | 54.5 |
| 6 | Black Inner capsules | 28 |

Example 10

Preparation of Double-Layer Cellulose Acetate Microcapsules Containing Yellow Iron Oxide (Cameleon Yellow Microcapsules)

MB was prepared as described in Example 8, using yellow inner capsules, as described in Example 3. Double layered microcapsules comprising black inner core were then prepared using an emulsion, extraction medium and process as described herein in Example 8.

The main components of the obtained microcapsules are presented in Table 15.

TABLE 15

| | Material | Loading for 100 grams |
|---|---|---|
| 1 | Cellulose Acetate | 7.5 |
| 2 | Acrylate/Ammonium Methacrylate Copolymer | 4.0 |
| 3 | Propylene Glycol Stearate | 4.0 |
| 4 | Magnesium Stearate | 2 |
| 5 | Titanium Dioxide | 54.5 |
| 6 | Yellow Inner capsules | 28 |

Example 11

Preparation of Double Layered Cellulose Acetate Microcapsules Containing Ferric Ammonium Ferrocyanide (Iron Blue) (Cameleon Blue Microcapsules)

Preparation of Organic Phase/Master Batch (MB) Stage:

An organic phase (herein referred to interchangeably as "master batch" (MB)) was prepared by gradually adding Cellulose Acetate under stirring into ethyl acetate under room temperature and stirring well until the mixture was homogeneous and transparent. Then Magnesium Stearate (MgSt) was added to the solution under stirring for about 5 minutes, followed by addition of Boron Nitrite (BN) under stirring for about 5 minutes. Titanium dioxide (TiO$_2$) was thereafter added to the solution under stirring for about 5 minutes and the obtained mixture was homogenized for about 8 minutes. Iron blue inners, prepared as described in U.S. Pat. No. 6,932,984 (with or without a plasticizer), were added to the mixture under stirring for about 5 minutes. The components and respective amounts of the MB ingredients are presented in Table 16.

TABLE 16

Master batch constituents

| Material | Loading for 100 grams MB |
|---|---|
| Cellulose Acetate | 6 |
| Magnesium Stearate | 2 |
| Boron Nitrite | 8.8 |
| Titanium Dioxide | 72 |
| Iron Blue inner capsules | 11.2 |
| Ethyl acetate | 233.3 |

Preparation of the Emulsion:

Emulsion was prepared by adding to water, while stirring, a 4% aqueous solution of Polyvinyl Alcohol (PVA), followed by a 4% aqueous solution of Ceteareth 25 (a polyoxyethylene ether, acting as an emulsifier, and thereafter adding to the aqueous phase ethyl acetate, under stirring for about 1-2 minutes. The MB described above was then gradually added into the emulsion under stirring at about 400 RPM for 2 minutes. The ratio between the Master Batch and the emulsion (w/w) was 1:3. The components and respective amounts of the emulsion are presented in Table 17.

TABLE 17

Emulsion constituents

| Material | Loading (grams) |
|---|---|
| Water | 910 |
| PVA | 90 |
| Ethyl Acetate | 100 |
| MB | 333.3 |

Extraction of the Organic Solvent:

The extraction medium was composed of a mixture of water and 4% aqueous solution of PVA (i.e., a final concentration of PVA in the extraction fluid was 0.2% PVA). The emulsion described above was gradually added into the extraction fluid in a 15 L pail under stirring at 150 RPM using a manual pump, and the obtained mixture was stirred for additional 15 minutes. The resulting mixture was left to sediment for about 24 hours at 25° C. The components and amounts of the extraction medium are presented in Table 18.

TABLE 18

Extraction medium constituents

| Material | Loading (grams) |
|---|---|
| Emulsion | 1333.3 |
| Water | 4178 |
| 4% PVA solution | 144 |

Washing, Drying and Sifting of the microcapsules was performed as described in Example 8.

The main components of the obtained microcapsules are presented in Table 19.

TABLE 19

| | Material | Loading for 100 grams |
|---|---|---|
| 1 | Cellulose Acetate | 6 |
| 2 | Magnesium Stearate | 2 |
| 3 | Boron Nitrite | 8.8 |
| 4 | Titanium Dioxide | 72 |
| 5 | Iron Blue inner capsules | 11.2 |

Example 12

Preparation of Double Layer Cellulose Acetate Microcapsules Containing Chromium Oxide Green (Cameleon Green Microcapsules)

MB was prepared as described in Example 8, using green inner capsules, containing Chromium Oxide green, prepared as described in U.S. Pat. No. 6,932,984 (with or without a plasticizer). Double layered microcapsules comprising green inner core were then prepared using an emulsion, extraction medium and process as described herein in Example 8.

The main components of the obtained microcapsules are presented in Table 20.

TABLE 20

| | Material | Loading for 100 grams |
|---|---|---|
| 1 | Cellulose Acetate | 5 |
| 2 | Acrylate/Ammonium Methacrylate Copolymer | 4 |
| 3 | Propylene Glycol Stearate | 6 |
| 4 | Magnesium Stearate | 2 |
| 5 | Titanium Dioxide | 49 |
| 6 | Green Inner capsules | 34 |

Example 13

Color Test Results (X-Rite)

The colors of the microcapsules of the present embodiments encapsulating either red, black or yellow colorants (herein termed RedCap New, Black Cap New and YellowCap New, respectively), and of commercial microcapsules encapsulating the same colorants (herein termed RedCap 1, Black Cap 1 and YellowCap 1), yet differing from the instant microcapsules by the process used for their preparation, as delineated herein, and by the absence of a fatty acid salt, were measured and specified.

A visual, qualitative comparative measurement of color lightness of formulations containing either microcapsules according to exemplary embodiments of the invention or commercial microcapsules as referred to herein, both containing the same colorants, is presented in FIGS. 1-4.

Figure 1:
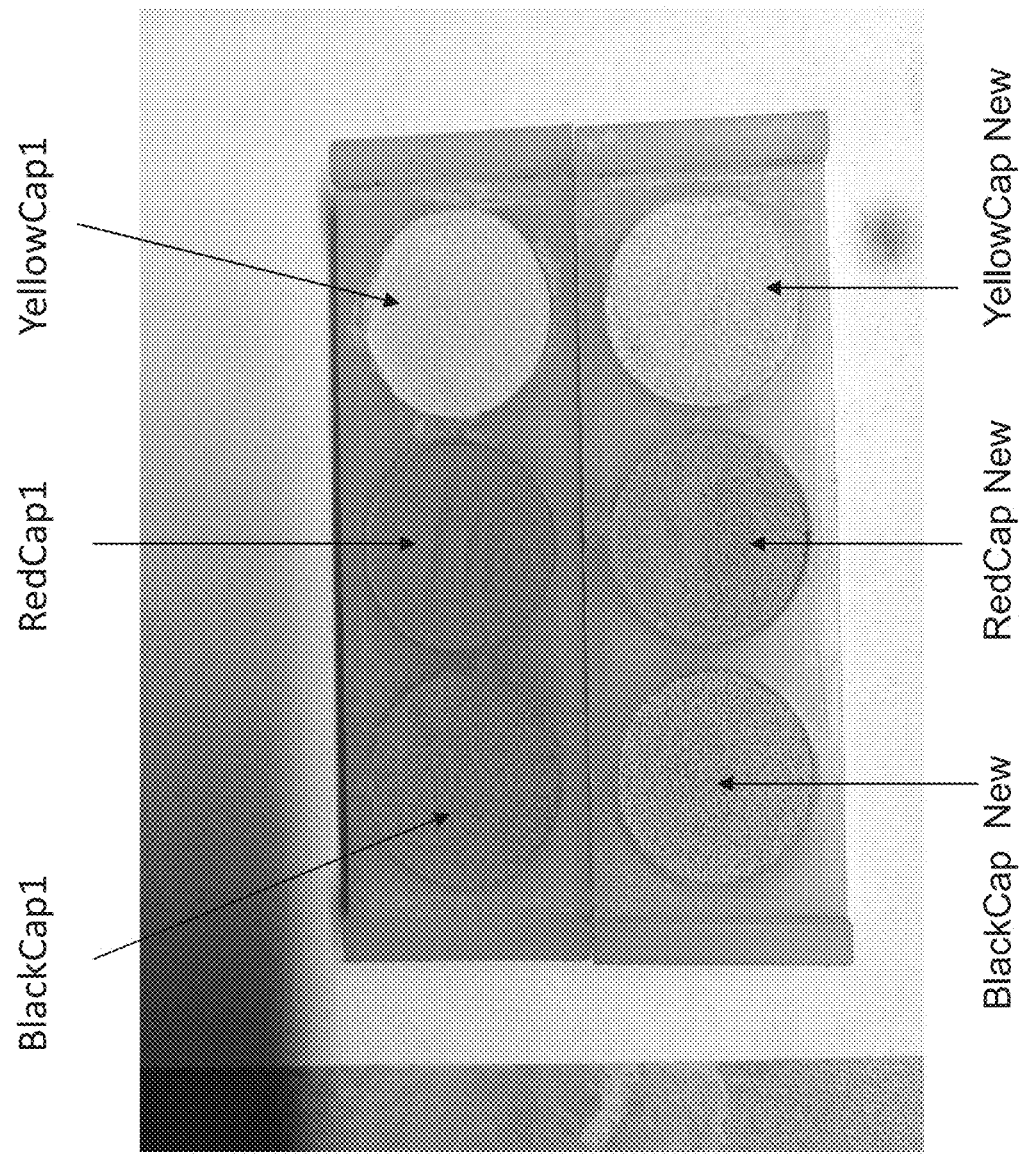

FIG. 1 presents 3 dishes containing powder that comprises commercial microcapsules encapsulating black, red or yellow colorants (upper dishes), known as "TagraCap1" (BlackCap1, RedCap1 and YellowCap1), and three dishes containing powders comprising the microcapsules of the invention, encapsulating the same black, red or yellow colorants (lower dishes), as described in Examples 5, 6 and 7.

FIG. 2 presents three pairs of vials, the left ones contain basic body lotion cream comprising exemplary color-containing microcapsules according to some embodiments of the invention (YellowCap New, RedCap New, Black Cap New), as described in Examples 5, 6 and 7, and the right ones contain the commercial microcapsules described herein (RedCap 1, Black Cap 1 and YellowCap 1).

As clearly seen in both FIGS. 1 and 2, powder formulations containing exemplary microcapsules according to some embodiments of the invention are substantially lighter and brighter than formulations containing the commercial microcapsules, particularly formulations comprising red and black colorants.

FIG. 3 presents 3 dishes containing powder that comprises commercial microcapsules encapsulating black, red or yellow colorants (upper dishes), known as "TagraCap1" (RedCap1, BlackCap1 and YellowCap1), and three dishes containing powders comprising the microcapsules of the invention, named CameleonCaps, encapsulating the same red, black or yellow colorants (lower dishes), as described in Examples 8, 9 and 10, respectively.

FIG. 4 presents three pairs of vials, the left ones contain basic body lotion cream comprising exemplary color-containing microcapsules according to some embodiments of the invention (Cameleon Red, Cameleon Black, Cameleon Yellow), as described in Examples 8, 9 and 10, and the right ones contain the commercial microcapsules described herein (RedCap 1, Black Cap 1 and YellowCap 1).

FIGS. 3 and 4 further demonstrate that powder formulations containing exemplary microcapsules according to some embodiments of the invention are substantially lighter and brighter than formulations containing the commercial microcapsules, particularly formulations comprising red and black colorants.

For quantitative color measurements, the X-Rite measurement technique using the CIE Color Systems (based on the CIE L*a*b* color scale, wherein L* defines lightness, a* denotes the red/green value and b* the yellow/blue value) was used. The standard illuminant applied for color measurements was daylight.

Quantitative color values were obtained by integrating values/data measured for three visual elements of color: hue (namely, how we perceive an object's color—red, orange, green, blue, and the like), chroma (the vividness or dullness of a color namely, how close the color is to either gray or the pure hue), and degree of lightness (namely classifying whether a color is light or dark). By describing a color using these three attributes, it is possible to accurately identify a particular color and distinguish it from any other.

Quantitative lightness values (L*) are presented in Tables 21 and 22 for exemplary microcapsules of the present embodiments and for commercial microcapsules, and the shift in lightness on the lightness scale L* of the present microcapsules relative to commercial ones is indicated (DL*). The positive DL* values presented in Tables 21 and 22 denote a shift on the lightness scale in the direction of substantially lighter, brighter color for the microcapsules of the invention compared to the commercial ones.

TABLE 21

| L* (lightness value) | Colorant/microcapsules | |
| --- | --- | --- |
| 56.1 | RedCap 1 | Red |
| 66.93 | RedCapNew (Example 5) | |
| 10.83 | DL* | |
| 58.25 | BlackCap1 | Black |
| 72.17 | BlackCap New (Example 6) | |
| 13.92 | DL* | |
| 76.52 | YellowCap1 | Yellow |
| 80.08 | YellowCapNew (Example 7) | |
| 4.28 | DL* | |

TABLE 22

| L* (lightness value) | Colorant/microcapsules | |
| --- | --- | --- |
| 59.83 | RedCap 1 | Red |
| 82.17 | CameleonRed (Example 8) | |
| 22.34 | DL* | |
| 59.91 | BlackCap1 | Black |
| 82.58 | CameleonBlack (Example 9) | |
| 22.67 | DL* | |
| 80.77 | YellowCap1 | Yellow |
| 86.85 | CameleonYellow (Example 10) | |
| 6.08 | DL* | |

FIGS. 5A-7B present the data obtained in the X-rite measurements.

FIGS. 5A, 6A and 7A present visual picture taken at similar photographing conditions) of the different powders containing the same colorant obtained from X-rite device, and showing the lighter and brighter visuality of a power containing microcapsules according to some embodiments of the present invention.

FIGS. 5B, 6B and 7B present comparative graphs showing the reflectance percentage (R %) at varying wavelength, and demonstrating the higher color-masking effect obtained by a powder containing microcapsules according to some embodiments of the present invention.

Example 14

Stability Test for a Gel Formulation

In order to assess the stability of the color-containing microcapsules of some exemplary embodiments of the present invention, a gel formulation was prepared by mixing carbomer, with water (1-1.5% carbomer by weight), and microcapsules (3% of total formulation weight) containing red, yellow or black colorant, as described in Examples 5, 6 and 7, respectively, were added to the carbomer gel and mixed therewith. The preparation was incubated at 40° C. for at least 3 months, while stirring at 2500 rpm. The color of the gel was monitored during incubation, and samples of the gel were taken and observed under light microscope. It was found that at least 90% of microcapsules thus observed maintained their shape even after 3 month incubation, and no leaking of color from the microcapsules to the gel was observed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A multi-layer microcapsule comprising an inner core microcapsule and at least one outer shell enveloping said inner core microcapsule, said inner core microcapsule comprising a core which comprises an active agent, said core being enveloped by a shell comprised of a first wall-forming material, and said at least one outer shell comprising a second wall forming material, an opaque substance and a fatty acid salt,
wherein:
each of said first and second wall-forming material independently comprises a polymer or copolymer selected from the group consisting of polyacrylate, a polymethacrylate, a cellulose ether, a cellulose ester, and any combination thereof;
said fatty acid salt comprising a fatty acyl derived from a fatty acid selected from the group consisting of stearic acid, arachidic acid, palmitoleic acid, oleic acid, linoleic acid, linolaidic acid, arachidonic acid, myristoleic acid and erucic acid, wherein an amount of said fatty acid salt ranges from about 0.05% to about 5%, or from about 0.1% to about 3%, or from about 0.2% to about 3%, or from about 0.5% to about 3%, or from about 0.5% to about 2.0%, or from about 1.0% to about 2.0%, % by weight, of the total weight of the microcapsule; and
an amount of said opaque substance ranges from about 10% to about 90% of the total weight of the microcapsule,
and wherein the multi-layer microcapsule is characterized by lightness values (L*) in the range of 60-100 on a lightness scale of an X-Rite measurement system.

2. The multi-layer microcapsule according to claim 1, wherein said at least one outer shell further comprises a plasticizer.

3. The multi-layer microcapsule according to claim 2, wherein said plasticizer is triethyl citrate.

4. The multi-layer microcapsule according to claim 2, wherein an amount of said plasticizer ranges from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 3.5% to about 6.0%, or from about 3.5% to about 5.5%, or from about 3.5% to about 5.0%, or is about 4.5% by weight, of the total weight of the microcapsule.

5. The multi-layer microcapsule according to claim 1, wherein said at least one outer layer further comprises a dispersing agent, capable of dispersing said active agent upon application on the skin.

6. The multi-layer microcapsule according to claim 5, wherein said dispersing agent is an ester of a fatty acid.

7. The multi-layer microcapsule according to claim 5, wherein an amount of said dispersing agent ranges s from about 0.5% to about 10%, or from about 0.5% to about 9.0%, or from about 1.0% to about 8.0%, or from about 1.0% to about 7.0%, or from about 1.5% to about 7.0%, or from about 1.5% to about 6.0%, or from about 2.0% to about 6.0%, or from about 2.5% to about 6.0%, or from about 3.0% to about 6.0%, or from about 3.5% to about 6.0%, or from about 4% to about 6%, of the total weight of the microcapsule.

8. The multi-layer microcapsule according to claim 1, wherein said opaque substance is $TiO_2$, and wherein an amount of $TiO_2$ ranges from about 10% to about 80%, or from about 30% to about 80%, or from about 30% to about 60%, by weight, of a total weight of the microcapsule.

9. The multi-layer microcapsule according to claim 1, wherein said fatty acid salt is magnesium stearate.

10. The multi-layer microcapsule according to claim 9, comprising magnesium stearate in an amount within a range of from 1.0% to about 2.0% by weight, $TiO_2$ in an amount within a range of from about 30% to about 75% by weight and a dispersing agent in an amount within a range of from about 4% to about 6% by weight, of the total weight of the microcapsule.

11. The multi-layer microcapsule according to claim 1, wherein said second wall forming material comprises a polymer or copolymer selected from the group consisting of an acrylate/ammonium methacrylate copolymer, cellulose acetate and a combination thereof.

12. The multi-layer microcapsule according to claim 1, comprising said inner core microcapsules in an amount ranging from about 10% to about 50% by weight, said second wall-forming polymer or copolymer in an amount ranging from about 5% to about 30% by weight, magnesium stearate in an amount ranging from about 0.5% to 1% by weight, $TiO_2$ in an amount ranging from about 25% to about 50% by weight and a dispersing agent in an amount ranging from about 1% to about 6%, by weight, of the total weight of the microcapsule.

13. The multi-layer microcapsule according to claim 1, being stable upon incubation in a gel formulation for at least 3 month at 40° C., while stirring.

14. A composition comprising a plurality of multi-layer microcapsules, at least a portion of said multi-layer microcapsules comprising a plurality of active agent-containing microcapsules according to claim 1.

15. A cosmetic or cosmeceutical formulation comprising the composition according to claim 14.

16. The cosmetic or cosmeceutical formulation according to claim 15, further comprising a cosmetically or cosmeceutically acceptable carrier.

17. The formulation according to claim 16, being an aqueous-based formulation and/or a gel formulation.

18. A process of preparing the multi-layer active agent-containing microcapsule according to claim 1, the process comprising:
(a) contacting a first organic phase comprising said second wall-forming polymer or copolymer, said fatty acid salt, optionally a dispersing agent, and a first partially water-miscible organic solvent with a first aqueous continuous phase saturated with said organic solvent and comprising an emulsifier, to thereby obtain a first multi-component emulsion, wherein either said first organic phase or said first aqueous phase further comprises said opaque substance and/or single-layer microcapsules, each of said single-layer microcapsules comprising said core comprising said least one active agent enveloped by said shell comprised of said first wall-forming material;

(b) adding to the formed emulsion an amount of water which initiates extraction of the organic solvent from the emulsion, thereby obtaining a double-layered microcapsule; and (c) optionally repeating steps (a) and (b), using a second, third, and so on, organic phases and aqueous continuous phases, thereby obtaining a multi-layered microcapsule, said fatty acid salt comprising a fatty acyl derived from a fatty acid selected from the group consisting of stearic acid, arachidic acid, palmitoleic acid, oleic acid, linoleic acid, linolaidic acid, arachidonic acid, myristoleic acid and erucic acid.

19. The process of claim 18, further comprising isolating the microcapsule following step (b).

20. The process according to claim 18, wherein said wall-forming polymer comprises acrylate/ammonium methacrylate copolymer, ethyl cellulose or a combination thereof; said organic solvent partially miscible with water is ethyl acetate; said dispersing agent is an ester of a fatty acid; said fatty acid salt is magnesium stearate and said opaque substance comprises titanium dioxide.

* * * * *